(12) United States Patent
Jauert et al.

(10) Patent No.: US 10,738,332 B2
(45) Date of Patent: Aug. 11, 2020

(54) GENETICALLY MODIFIED YEASTS AND FERMENTATION PROCESSES USING GENETICALLY MODIFIED YEASTS

(71) Applicant: CARGILL, INCORPORATED, Wayzata, MN (US)

(72) Inventors: Peter Alan Jauert, Minneapolis, MN (US); Genfeng Lu, Edina, MN (US); Gregory M. Poynter, St. Paul, MN (US); Brian J. Rush, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/778,881

(22) PCT Filed: Nov. 22, 2016

(86) PCT No.: PCT/US2016/063406
§ 371 (c)(1),
(2) Date: May 24, 2018

(87) PCT Pub. No.: WO2017/091614
PCT Pub. Date: Jun. 1, 2017

(65) Prior Publication Data
US 2018/0346937 A1 Dec. 6, 2018

Related U.S. Application Data

(60) Provisional application No. 62/259,531, filed on Nov. 24, 2015.

(51) Int. Cl.
*C12P 7/56* (2006.01)
*C12P 7/14* (2006.01)
*C12P 7/06* (2006.01)
*C12N 15/81* (2006.01)

(52) U.S. Cl.
CPC ............. *C12P 7/14* (2013.01); *C12N 15/815* (2013.01); *C12P 7/06* (2013.01); *C12P 7/56* (2013.01); *C12Y 302/01026* (2013.01); *C12Y 503/01005* (2013.01); *Y02E 50/17* (2013.01)

(58) Field of Classification Search
CPC ............. C12P 7/14; C12P 7/56; C12N 15/815
See application file for complete search history.

(56) References Cited

U.S. PATENT DOCUMENTS

| | | | |
|---|---|---|---|
| 5,876,988 A | 3/1999 | Selten et al. | |
| 8,097,448 B2 * | 1/2012 | Suominen | C12P 7/56 435/137 |
| 2007/0031950 A1 | 2/2007 | Winkler | |
| 2012/0171719 A1 | 7/2012 | Hong et al. | |
| 2012/0214214 A1 | 8/2012 | Hara et al. | |
| 2014/0038253 A1 | 2/2014 | Jessen et al. | |
| 2014/0256048 A1 | 9/2014 | Chen et al. | |

FOREIGN PATENT DOCUMENTS

| | | |
|---|---|---|
| WO | 9914335 A1 | 3/1999 |
| WO | 0071738 A1 | 11/2000 |
| WO | 0242471 A2 | 5/2002 |
| WO | 20040993812 A2 | 11/2004 |
| WO | WO2007032792 * | 3/2007 |
| WO | 2010074577 A1 | 7/2010 |
| WO | 2012087964 A1 | 6/2012 |
| WO | 2014018757 A1 | 1/2014 |
| WO | 2017091610 A1 | 6/2017 |
| WO | 2017091614 A1 | 6/2017 |

OTHER PUBLICATIONS

Sreekrishna et al. 1987; Invertase gene (SUC2) of *Saccharomyces cerevisiae* as a dominant marker for transformation of Pichia pastoris. Gene. 59(1): 115-125. Abstract Only.*
Radecka et al. Jun. 30, 2015; Looking beyond *Saccharomyces*: the potential of non-conventional yeast species for desirable traits in bioethanol fermentation. FEMS Yeast Research. 15: 1-13.*
UCdavis, Viticulture & Enology. Issatchenkia orientalis. 2018. On the web at: wineserver.ucdavis.edu/industry-info/enology/wine-microbiology/yeast-mold/issatchenkia-orientalis.*
Feng, et al., "The Relationship between Fermentation Activity of *Saccharomyces cerevisiae* in High-sugar Dough and Sucrase Activity", Modern Food Science and Technology, vol. 30, No. 5, 2014, 131-135.
Förster, André, et al., "Citric acid production from sucrose using a recombinant strain of the yeast *Yarrowia lipolytica*", Applied Microbiology and Biotechnology, Springer, Berlin, DE—ISSN 1432-0614 vol. 75, Issue 6. XP019513772, Apr. 20, 2007, 1409-1417.
Georis, et al., "Glucose repression of the Kluyveromyces lactis invertase gene K/INVi does not require Migip", Molecular and General Genetics, vol. 261, No. 4-5. XP008183240, Jun. 1999, 862-870.
H P Hsieh, "An autoselection system in recombinant Kluyveromyces lactis enhances cloned gene stability and provides freedom in medium selection", XP055304987, Retrieved from the Internet: URL:http://rd.springer.com/content/pdf/10, Jan. 1, 1998, 147-152.
Jessica CM Gallardo, et al., "Enrichment of a continuous culture of *Saccharomyces cerevisiae* with the yeast *Issatchenkia orientalis* in the production of ethanol at increasing temperatures", Journal of Industrial Microbiology & Biotechnology : Official Journal of the Society for Industrial Microbiology. Springer, Berlin, DE, vol. 38, No. 3, XP019883458, Aug. 10, 2010, 405-414.
Jessica CM Gallardo, et al., "Ethanol production from molasses in co-culture of Issatchenkia orientalis and *Saccharomyces cerevisiae* at 42° C.", XP055344048 Retrieved from the Internet: URL:http://conferencing.uwex.edu/conferences/icy2012/documents/ArealPosters.pdf, Aug. 26, 2012, 62.
Lazar, Zbigniew, et al., "Optimized invertase expression and secretion cassette for improving Yarrowia lipolytica growth on sucrose for industrial applications", J Ind Microbiol Biotechnol. 2013; 40(11) Published online: doi: 10.1007/s10295-013-1323-1, Sep. 6, 2013, 1273-1283.

(Continued)

*Primary Examiner* — Karen Cochrane Carlson

(57) ABSTRACT

The present invention relates to a genetically engineered yeast capable of manufacturing a fermentation product using sucrose as a fermentation substrate, and fermentation processes using such a yeast. In some embodiments, the fermentation product is ethanol.

20 Claims, No Drawings

Specification includes a Sequence Listing.

(56) References Cited

OTHER PUBLICATIONS

Leonardo De Figueiredo Vilela, et al., "Functional expression of Burkholderia cenocepacia xylose isomerase in yeast increases ethanol production from a glucose-xylose blend", Bioresource Technology vol. 128. XP055278232, Oct. 16, 2012, 792-796.

Rajoka, et al., "Kinetics and thermodynamics of ethanol production by a thermotolerant mutant of *Saccharomyces cerevisiae* in a microprocessor-controlled bioreactor", Letters in Applied Microbiology vol. 40, No. 5. XP055344147, May 1, 2005, 316-321.

Siso, et al., "Respirofermentative metabolism in Kluyveromyces lactis: Ethanol production and the Crabtree effect.", 1996; Enzymes and Microbiology Technology. 18: 585-591.

Higuchi, R., "PCR Protocols: A Guide to Methods and Applications", A.I Michael, D.H. Gelfand, D.J. Sninsky and T.J. White (eds.), Academic Press, pp. 177-183, 1990.

Bernhard, Susan L., et al., "Cysteine Analogs of Recombinant Barley Ribsosome Inactivating Protein Form Antibody Conjugates with Enhanced Stability and Potency in Vitro", Bioconjugate Chem. 1994, 5, 126-132.

Brat, Dawid, et al., "Functional Expression of a Bacterial Xylose Isomerase in *Saccharomyces cerevisiae*", Applied and Environmental Microbiology, Apr. 2009, p. 2304-2311.

De Deken, R. H., "The Crabtree Effect: a Regulatory System in Yeast", J. gen. Microbiol. (1966), 44, 149-156.

Gietz, Daniel, et al., "Improved method for high efficiency transformation of intact yeast cells", Nucleic Acids Research, vol. 20, No. 6, 1425.

Han, Byeong-Gu. et al., "Crystal structure of a class 2 D-xylose isomerase from the human intestinal tract microbe Bacteroides thetaiotaomicron", Biodesign, vol. 3, No. 1, pp. 41-47, 2015.

Ito, Wataru, et al., "A general method for introducing a series of mutations into cloned DNA using the polymerase chain reaction", Gene, 102 (1991) 67-70.

Kurtzman, Cletus P., et al., "Identification and phylogeny of ascomycetous yeasts from analysis of nuclear large subunit (26S) ribosomal DNA partial sequences", Antonie van Leeuwenhoek, vol. 73, 1998, 331-371.

Kurtzman, Cletus P., et al., "The Yeasts, A Taxonomic Study", Fourth Edition, Section 35, Issatchenkia Kudryavtsev, 1998, 222-223.

Kuyper, M, et al., "High-level functional expression of a fungal xylose isomerase: the key to efficient ethanolic fermentation of xylose by *Saccharomyces cerevisiae*", FEMS Yeast Research, Wiley-Blackwell Publishing Ltd, GB, NL, vol. 4 No. 1, XP002312913, Oct. 1, 2003, 69-78.

Lee, Sun-Mi, et al., "Directed Evolution of Xylose Isomerase for Improved Xylose Catabolism and Fermentation in the Yeast *Saccharomyces cerevisiae*", AEM, vol. 78, No. 16, pp. 5708-5716, Aug. 2012.

Lee, Sun-Mi, et al., "Systematic and evolutionary engineering of a xylose isomerase-based pathway in *Saccharomyces cerevisiae* for efficient conversion yields", Biotechnology for Biofuels 2014, 7:122.

Nielsen, Jens, et al., "Bio action Engineering Principles", Second Edition, Kluwer Academic/Plenum Publishers, equation 1, 2003, 449.

Silveira. M.C.F., et al., "Assay for in Vivo Yeast Invertase Activity Using NaF", Analytical Biochemistry 238, 26-28 (1996).

Terpe, K., Overview of tag protein fusions: from molecular and biochemical fundamentals to commercial systems. Appl Microbiol Biotechnol 60, 523-533 (2003). https://doi.org/10.1007/s00253-002-1158-6.

Vallette, Francois, et al., "Construction of mutant and chimeric genes using the polymerase chain reaction", Nucleic Acids Research, vol. 17, Issue 2, Jan. 25, 1989, pp. 723-733, https://doi.org/10.1093/nar/17.2.723.

Vangrysperre, W., et al., "Single active-site histidine in D-xylose isomerase from Streptomyces violaceoruber", Biochem J. 263. 1989, 195-199.

Verduyn, Cornelis, et al., "Effect of Benzoic Acid on Metabolic Fluxes in Yeasts: A Continuous-Culture Study on the Regulation of Respiration and Alcoholic Fermentation", Yeast, vol. 8, 1992, 501-517.

\* cited by examiner

GENETICALLY MODIFIED YEASTS AND FERMENTATION PROCESSES USING GENETICALLY MODIFIED YEASTS

CROSS-REFERENCE TO RELATED APPLICATIONS

This application is a national phase application of international application PCT/US2016/063406, filed Nov. 22, 2016, and entitled GENETICALLY MODIFIED YEASTS AND FERMENTATION PROCESSES USING GENETICALLY MODIFIED YEASTS, which application claims the benefit of U.S. Provisional Patent Application Ser. No. 62/259,531, filed on Nov. 24, 2015, entitled GENETICALLY MODIFIED YEASTS AND FERMENTATION PROCESSES USING GENETICALLY MODIFIED YEASTS, both of which applications are hereby incorporated by reference herein in their entirety.

SEQUENCE LISTING

The entire contents of the ASCII text file entitled "N00316_US_PCT[3]_ST25.txt ," created on May 24, 2018, and having a size of 41 kilobytes is incorporated herein by reference in its entirety.

BACKGROUND OF THE INVENTION

Industrial yeast fermentation processes often use glucose-based substrates in regions of the world where such substrates are readily available. For example, glucose syrup made from corn starch is commonly used in fermentation processes in the United States. However, in some regions, sucrose substrates are more readily available and/or more economical for use in fermentation processes, or it is desirable to use such sucrose substrates as a supplement to glucose substrates.

SUMMARY OF THE INVENTION

Described herein are genetically engineered yeasts for manufacturing fermentation products and fermentation processes based on the use of such yeasts. In one aspect, the present invention relates to a genetically engineered yeast capable of manufacturing ethanol, comprising: a yeast having a functional heterologous invertase gene and a heterologous xylose isomerase gene, wherein the yeast is capable of producing ethanol at a rate of at least $0.7$ g $L^{-1}$ $h^{-1}$, and the genetically engineered yeast is engineered from a host yeast wherein the wild-type of the host yeast does not include a functional invertase gene.

In some embodiments, the yeast is capable of an ethanol production rate of at least $1.0$ g $L^{-1}$ $h^{-1}$. In some embodiments, the yeast is capable of an ethanol production rate of at least $1.5$ g $L^{-1}$ $h^{-1}$. In some embodiments, the yeast is capable of producing ethanol at a pathway fermentation yield of at least 35 percent. In some embodiments, the yeast is capable of producing ethanol at a pathway fermentation yield of at least 40 percent. In some embodiments, wherein the yeast is capable of producing ethanol at a pathway fermentation yield of at least 45 percent. In some embodiments, the yeast is capable of producing ethanol at a pathway fermentation yield of at least 50 percent. In some embodiments, the yeast is capable of producing ethanol at a pathway fermentation yield in the range of 35-50 percent. In some embodiments, the yeast is capable of producing ethanol at a final titer of at least 30, 35, 40, 45, 50, 55, 60, 65, 70, 75, 80, 85, 90, 95, or 100 g/liter.

In some embodiments, the host yeast is a yeast of the *I. orientalis/P. fermentans* clade. In some embodiments, the host yeast is *I. orientalis*. In some embodiments, the yeast is Crabtree-negative. In some embodiments, the functional invertase gene is selected from the group consisting of SEQ ID NO: 1; SEQ ID NO: 2; SEQ ID NO: 3; and SEQ ID NO: 4. In some embodiments, the yeast further comprises an exogenous or artificial promoter for the functional invertase gene. In some embodiments, the promoter is selected from the group consisting of Pyruvate decarboxylase, Glyceraldehyde-3-phosphate dehydrogenase, Translational elongation factor, Transaldolase, RPL16B, 3-phosphoglycerate kinase, and Enolase.

In one aspect, the present invention relates to processes for manufacturing a bioproduct using a yeast including a functional exogenous invertase gene. In some embodiments, the process is a process for manufacturing ethanol comprising fermenting a substrate using any of the yeasts having an exogenous invertase gene described herein. In some embodiments, the substrate comprises sucrose. In some embodiments, the substrate comprises xylose. In some embodiments, the substrate comprises sucrose and xylose. In some embodiments, the substrate comprises one or more materials from a sucrose-processing process, including but not limited to: sucrose, bagasse, and/or molasses.

In some embodiments, the process is a process for manufacturing ethanol, comprising: consuming a substrate using a genetically engineered yeast, wherein the yeast comprises an exogenous invertase gene and an exogenous xylose isomerase gene, and the substrate comprises sucrose. In some embodiments, the substrate further comprises a pentose. In some embodiments, the process is a yeast seed growth process for producing an amount of yeast seed. In some embodiments, the process further comprises inoculating a fermentation medium comprising a pentose with a portion of the yeast seed. In some embodiments, the process further comprises adding sucrose to the fermentation medium before, during, and/or after inoculating.

In some embodiments, the yeast is a yeast of the *I. orientalis/P. fermentans* clade. In some embodiments, the yeast is *I. orientalis*. In some embodiments, the process is microaerobic. In some embodiments, the fermentation media comprises hydrozylates of starch. In some embodiments, the fermentation media comprises lignocellulosic hydrozylates.

In some embodiments, the volumetric oxygen uptake rate (OUR) is 1 to 10 mmol $O_2$/(L·h). In some embodiments, the fermentation cell concentration is 1 to 10 g cell dry weight/L. In some embodiments, the fermentation cell concentration is 2 to 8 g cell dry weight/L. In some embodiments, the fermentation cell concentration is 2.5 to 6 g cell dry weight/L. In some embodiments, the fermentation cell concentration is at least 20 g cell dry weight/L. In some embodiments, the pitch density is 0.05 to 5 g cell dry weight/L. In some embodiments, the pitch density is 0.05 to 4 g cell dry weight/L. In some embodiments, the pitch density is 0.05 to 2 g cell dry weight/L. In some embodiments, the fermentation temperature is in the range of 25 to 45° C. In some embodiments, the fermentation temperature is in the range of 20 to 40° C. In some embodiments, the fermentation temperature is in the range of 33 to 38° C. In some embodiments, the pathway fermentation yield is at least 35, 40, 45, or 50 percent. In some embodiments, the final titer is at least 30, 35, 40, 45, 50, 55, 60, 65, 70, 75, 80, 85, 90, 95, or 100 g/liter g/liter. In some embodiments, the yeast for any process embodiment is any yeast embodiment described herein.

It is also to be understood that the elements or aspects of any embodiment of the processes, methods, or compositions described above can be applied to any other embodiment, as would be understood by a person skilled in the art.

DETAILED DESCRIPTION

It is to be understood that the figures and descriptions of the present invention provided herein have been simplified to illustrate elements that are relevant for a clear understanding of the present invention, while eliminating other elements found in the related field(s) of art. Those of ordinary skill in the art would recognize that other elements or steps may be desirable or required in implementing the present invention. However, because such elements or steps are well known in the art or do not facilitate a better understanding of the present invention, a discussion of such elements or steps is not provided herein.

Definitions

Unless defined otherwise, all technical and scientific terms used herein have the same meaning as commonly understood by one skilled in the art to which this invention belongs. As used herein, each of the following terms has the meaning associated with it as defined in this section.

Fermentation Process Definitions

As used herein, "inoculation" is defined as the point in time wherein a microorganism capable of producing a fermentation product is introduced into a fermentation medium. This is a term that is well known to those skilled in the art.

As used herein, "end of fermentation" is defined as the point in time where a fermentation process meets a predetermined criteria. The predetermined criteria can include any of the following: a predetermined time interval, exhaustion of the desired fraction of carbon source supplied, cessation of carbon source consumption, or cessation of fermentation product formation. In one embodiment, "end of fermentation" is defined as the point in time where harvesting of the bioproduct is started. As would be understood by a person skilled in the art, "end of fermentation" can refer to a point in time that is different depending on the scale and purpose of the fermentation process. For a large-scale production fermentation process, the "end of fermentation" is preferably the point at which harvesting of the bioproduct is started, i.e., after product formation has effectively stopped.

As used herein, "cell dry weight" refers to the concentration of dry cell mass present in a fermentation medium at the time of measurement, as measured in a fermentation sample. Cell dry weight is commonly expressed in units of grams/liter (g/L).

As used herein, "cell dry weight at inoculation" refers to the concentration of dry cell mass present in a fermentation medium immediately following inoculation, as measured in a fermentation sample. For fed-batch fermentations, the initial cell dry weight is calculated based on the final volume of fermentation medium. Measurement of dry cell weight is a method known to those skilled in the art. Cell dry weight at inoculation is commonly expressed in units of g/L.

As used herein, "cell dry weight at end of fermentation" refers to the concentration of dry cell mass present in a fermentation medium at the end of fermentation, as measured in a fermentation sample. Cell dry weight at end of fermentation is commonly expressed in units of g/L.

As used herein, "final titer" refers to the concentration of a substance in the fermentation broth at the end of fermentation. The final titer is commonly expressed in units of g/L.

As used herein, "initial titer" refers to the concentration of a substance present at inoculation. The initial titer is commonly expressed in units of g/L.

As used herein, "batch time" refers to the amount of time that has elapsed between the inoculation and the end of fermentation. The batch time is commonly expressed in units of hours (h).

As used herein, "sugar consumption rate" for a batch process refers to the difference between the initial titer of a sugar present in the fermentation broth and the final titer of the same sugar (initial titer minus final titer) divided by the batch time. The sugar consumption rate is commonly expressed in units of grams per liter-hour (g $L^{-1}$ $h^{-1}$, which can also be abbreviated as (g/(L*h))). When applied to a continuous or semi-continuous process, the "sugar consumption rate" is determined using methods known in the art.

As used herein, the "specific sugar consumption rate" for a batch process refers to the sugar consumption rate divided by the cell dry weight at the end of fermentation. The specific sugar consumption rate is commonly expressed in units of (g sugar) (g cells)$^{-1}$ $h^{-1}$. When applied to a continuous or semi-continuous process, the "specific sugar consumption rate" is determined using methods known in the art.

The sugar consumption rate and specific sugar consumption rate may be applied to specific sugars such as, for instance, glucose or sucrose. In these cases, one may refer to a glucose consumption rate, specific glucose consumption rate, sucrose consumption rate, or specific sucrose consumption rate.

As used herein, "fermentation production rate" for a batch process refers to the final titer minus initial titer of fermentation product (final titer minus initial titer) divided by the batch time. The production rate is commonly expressed in units of grams per liter-hour (g $L^{-1}$ $h^{-1}$). When applied to a continuous or semi-continuous process, the "fermentation production rate" is determined using methods known in the art.

As used herein, the "specific production rate" refers to the fermentation production rate divided by the cell dry weight at the end of fermentation. The specific production rate is commonly expressed in units of (g product) (g cells)$^{-1}$ $h^{-1}$. When applied to a continuous or semi-continuous process, the "specific production rate" is determined using methods known in the art.

As used herein, "product yield" of a fermentation product refers to a ratio of two quantities: a) mass of product (e.g., succinate) produced in the course of the fermentation (numerator) b) the mass of carbon source added to the fermentation (denominator). The product yield as a percentage is commonly expressed in units of gram per gram (g/ g) times 100. Particular note should be taken that product yield is calculated as a ratio of masses. The mass of fermentation product produced should account for the mass of fermentation product present in the fermentation medium at the end of the batch, as well as the mass of any fermentation product harvested during the course of the batch, less the mass of fermentation product present at the start of batch, and further less the mass of any fermentation product added during the course of the batch. The mass of carbon source added to the batch should include the mass of all carbon source(s) present in the fermenter at the start of the batch in addition to the mass of any carbon source(s) added during the course of the batch.

As used herein, "oxygen uptake rate" ("OUR") refers to the volumetric rate at which oxygen is consumed during a fermentation. Inlet and outlet oxygen concentrations can be measured with exhaust gas analysis, for instance by mass spectrometers. OUR can be calculated by one of ordinary skill in the relevant arts using the Direct Method described in Bioreaction Engineering Principles 2nd Edition, 2003, Kluwer Academic/Plenum Publishers, p. 449, equation 1. It is commonly measured in units of (mmol $O_2$) $L^{-1}$ $h^{-1}$.

As used herein, "specific oxygen uptake rate" refers to the specific rate at which oxygen is consumed during a fermentation. It is calculated as the ratio of the OUR to the measured cell dry weight. It is commonly measured in units of mmol $O_2$ (g cell dry weight)$^{-1}$ $h^{-1}$.

As used herein, the term "microaerobic" refers to fermentation aeration conditions that are intermediate between fully aerobic and anaerobic conditions. Under microaerobic conditions, oxygen is supplied to the fermentation. Further, the oxygen is supplied at a rate such that the dissolved oxygen concentration is predominantly maintained below 5% of the saturation concentration of oxygen in the fermentation medium under air at atmospheric pressure. Under microaerobic conditions, the oxygen uptake rate is typically between 0.1 (mmol $O_2$) $L^{-1}$ $h^{-1}$ and 40 (mmol $O_2$) $L^{-1}$ $h^{-1}$ Yeast Characteristics Definitions As used herein, the term "Crabtree-negative" refers to a yeast cell having a Crabtree-negative phenotype, i.e., any yeast cell that does not exhibit the Crabtree effect. In one embodiment, the host cell of the present invention is a Crabtree-negative yeast. The Crabtree effect concerns the inhibition of synthesis of respiratory enzymes. The Crabtree effect is defined as the occurrence of fermentative metabolism under aerobic conditions as a result of the inhibition of oxygen consumption by a microorganism when cultured at high specific growth rates (long-term effect) or in the presence of high concentrations of glucose (short-term effect). Organisms with the Crabtree negative phenotype do not exhibit this effect, and are thus able to consume oxygen even in the presence of high concentrations of glucose or at high growth rates. Whether an organism is Crabtree positive or Crabtree negative can be determined by comparing the ratio of fermented glucose to respired glucose during cultivation under aerobic conditions, with a ratio of greater than 1 indicative of a Crabtree positive organism (e.g., see De Deken, R. H. (1965) J. gen. Microbiol., 44:149-156).

In certain embodiments, the genetically modified yeast cells provided herein further comprise a deletion or disruption of one or more native genes. As used herein, the phrase "deletion or disruption" with regard to a native gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 90% reduction) of an active enzyme, or produces an enzyme with severely reduced (at least 75% reduced, preferably at least 90% reduced) activity.

In certain embodiments, deletion or disruption of one or more native genes results in a deletion or disruption of one or more native metabolic pathways. The phrase "deletion or disruption" with regard to a metabolic pathway means that the pathway is either inoperative or else exhibits activity that is reduced by at least 75%, at least 85%, or at least 95% relative to the native pathway. In certain embodiments, deletion or disruption of a native metabolic pathway is accomplished by incorporating one or more genetic modifications that result in decreased expression of one or more native genes that reduce ethanol production.

In some embodiments, deletion or disruption of native genes can be accomplished by forced evolution, mutagenesis, or genetic engineering methods, followed by appropriate selection or screening to identify the desired mutants. In some embodiments, deletion or disruption of a native host cell gene can be coupled to the incorporation of one or more exogenous genes into the host cell, i.e., the exogenous genes can be incorporated using a gene expression integration construct that is also a deletion construct. In some embodiments, deletion or disruption can be accomplished using a deletion construct that does not contain an exogenous gene or by other methods known in the art.

The term "exogenous" as used herein with regard to genetic components means that the genetic component is present in a modified version of a microorganism, but is not present in the genome of a native form of the particular microorganism cell. In some embodiments, the exogenous genetic component can be a modified form of a component that was native to the cell, it can be derived from another organism, it can be a modified form of a component derived from another organism, or it can be a synthetically-derived component. For example, the *K. lactis* invertase gene is exogenous when introduced into *I. orientalis*.

Inspection of nucleic acid or amino acid sequences for two nucleic acids or two polypeptides will reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 7 should be considered to have specifically disclosed subranges such as from 1 to 3, from 1 to 4, from 1 to 6, from 2 to 5, from 3 to 5, etc., as well as individual numbers within that range, for example, 1, 2, 3, 3.6, 4, 5, 5.8, 6, 7, and any whole and partial increments in between. This applies regardless of the breadth of the range.

Description

Described herein are genetically modified yeast strains useful for manufacturing a fermentation product and fermentation processes using these yeasts. The yeast strains are modified to include a functional exogenous invertase gene. Accordingly, in one embodiment, the present invention relates to a yeast strain useful for fermentation processes having sucrose as a substrate. In some embodiments, the yeast can be used to manufacture an alcohol. In some embodiments, the yeast can be used to produce ethanol from sucrose-containing substrates at commercially useful rates and/or titers. In some embodiments, the yeast can further include a gene for xylose isomerase expression, wherein the yeast can be useful for fermentation processes having xylose as a substrate. In one embodiment, the yeast is Crabtree negative.

As contemplated herein, sucrose-based fermentation processes would preferably use a yeast expressing the invertase enzyme. However, invertase expression is not native to many yeasts that are desirable for industrial fermentation processes. Feng et al., describe the relationship between the fermentation activity of Saccharomyces cerevisiae in high-sugar dough and sucrase activity (Modern Food Sci. and Tech., 2014, 30:131-135). However, Saccharomyces cerevisiae may not be a useful host yeast for fermentation processes using certain substrates, for example, substrates containing cellulose or hemicellulose. In one aspect, the yeast is useful for producing ethanol a fermentation medium containing any material associated with the processing of sugar cane.

Genetically Engineered Yeast

The genetically modified yeast of the present invention is made by performing one or more genetic modifications to a host yeast cell. In some embodiments, the host yeast cell lacks a native invertase gene. In some embodiments, the host yeast cell does not include a nucleic acid encoding a polypeptide with a sequence that has greater than 70% identity with SEQ ID NO: 1, SEQ ID NO: 2, SEQ ID NO: 3, or SEQ ID NO: 4. In some embodiments, the host yeast cell cannot grow on sucrose as a sole carbon source. In some embodiments, the host yeast cell has a maximum specific growth rate on (YNB+20 g/L glucose) media that exceeds 0.15 $h^{-1}$ and a maximum specific growth rate on (YNB+20 g/L sucrose) media that is less than 0.05 $h^{-1}$. In some embodiments, the host yeast is a Crabtree-negative yeast. In some embodiments, the host yeast cell lacks a native xylose isomerase gene. In some embodiments, the host yeast cell lacks both a native invertase gene and a native xylose isomerase gene.

In some embodiments, the genetically modified yeast cells described herein belong to, or are derived from a host cell belonging to, the genus Issatchenkia, and in some such embodiments the yeast cells are I. orientalis. When first characterized, the species I. orientalis was assigned the name Pichia kudriavzevii. I. orientalis yeasts have also been described in the art as C. krusei. Numerous additional synonyms for the species I. orientalis have been described (see Kurtzman and Fell, The Yeasts, a Taxonomic Study, Section 35, Issatchenkia Kudryavtsev, pp. 222-223 (1998), which is hereby incorporated by reference).

The I. orientalis/P. fermentans clade is the most terminal clade that contains at least the species I. orientalis, Pichia galeiformis, Pichia sp. YB-4149 (NRRL designation), Candida ethanolica, Pichia deserticola, P. membranifaciens, and P. fermentans. Members of the I. orientalis/P. fermentans clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," Antonie van Leeuwenhoek 73:331-371, 1998, which is hereby incorporated by reference (see especially p. 349). Analysis of the variable D1/D2 domain of the 26S ribosomal DNA from hundreds of ascomycetes has shown that the I. orientalis/P. fermentans clade contains very closely related species. Members of the I. orientalis/P. fermentans clade exhibit greater similarity in the variable D1/D2 domain of the 26S ribosomal DNA to other members of the clade than to yeast species outside of the clade. Therefore, other members of the I. orientalis/P. fermentans clade can be identified by comparison of the D1/D2 domains of their respective ribosomal DNA, and comparing to that of other members of the clade and closely related species outside of the clade, using Kurtzman and Robnett's methods.

As described herein, the present invention relates to genetically modified yeasts of the I. orientalis/P. fermentans clade, preferably I. orientalis. However, the present invention is not limited to using any specific yeast such as I. orientalis, and the host yeast cell can be any suitable yeast strain, as would be understood by a person skilled in the art. To genetically modify the yeast cell, a suitable locus is selected for gene integration. One of ordinary skill in the art would know how to select suitable loci in a yeast genome for gene integration. An example of a suitable locus for integration of exogenous genes in I. orientalis includes, but is not limited to, locus A, which is flanked by SEQ ID NO: 5 and SEQ ID NO: 6. Further, one of ordinary skill in the art would recognize how to use sequences to design PCR primers to verify correct gene integration at the chosen locus.

As contemplated herein, the genetically modified or engineered yeast of the present invention includes a functional exogenous invertase expression gene. In one embodiment, the genetically modified yeast can include more than one copy of a functional invertase expression gene. For example, a diploid yeast can include an invertase gene copy on each chromosome. In some embodiments, the genetically modified yeast can include one or more additional exogenous integrated genes other than the functional invertase expression gene. In another embodiment, the genetically modified yeast can include a functional sucrase gene instead of, or in addition to, the invertase gene. In some embodiments, the host yeast cell can include a xylose isomerase gene. An example of a xylose isomerase-modified yeast strain and a method for modifying a yeast to include such a heterologous xylose isomerase gene is described in International Application No. PCT/US2016/045579, filed Aug. 4, 2016, which is hereby incorporated by reference in its entirety. As would be understood by a person skilled in the art, the yeast of the present invention can include any heterologous xylose isomerase gene, and is not limited to the specific xylose isomerase-modified yeast gene and method for modifying a yeast to include such a heterologous xylose isomerase gene described therein.

Exemplary invertase expression genes suitable for gene integration in a yeast strain include, but are not limited to:

an invertase gene from *K. lactis* (KlINV); *S. cerevisiae* (ScSUC2); *Schizosaccharomyces pombe* (inv1); and *Aspergillus niger* (invA) also identified as SEQ ID NO: 1; SEQ ID NO: 2; SEQ ID NO: 3; and SEQ ID NO: 4, respectively.

The genetically modified yeast of the present invention can also include exogenous or artificial promoters for the functional exogenous invertase expression gene or any other gene integrated into the yeast. One skilled in the art would know how to select and integrate suitable promoters into the host yeast cell. Examples of suitable promoters include, but are not limited to the promoters for the following *I. orientalis* genes: Pyruvate Decarboxylase (PDC), Glyceraldehyde-3-phosphate dehydrogenase (TDH3), Translational elongation factor (TEF), Transaldolase (TAL), RPL16B, 3-phosphoglycerate kinase (PGK), and Enolase (ENO).

In some embodiments, the integrated functional exogenous invertase expression may be associated with invertase activity which, once integrated into the host yeast cell, can be significantly greater than the desirable or optimal invertase activity. Greater than desired invertase activity can result in a less than optimal fermentation process. Greater than desired invertase activity can be problematic for a host cell and result in a reduction in the sugar consumption rate of the cell. While not wishing to be bound by theory, this reduction in sugar consumption rate can be due to the metabolic burden associated with producing large quantities of invertase protein, or can be due to other reasons that are not well understood.

Accordingly, the present invention also relates to the adjustment of invertase expression associated with the genetically modified yeast. Invertase expression in the genetically modified yeast can be optimized through one or more techniques known in the art. For example, in one embodiment, the amino acid sequence of invertase can be modified to reduce activity. In another embodiment, promoters associated with lower expression of invertase can be identified and integrated into the host yeast. However, the methods and compositions for optimizing invertase expression are not limited to those described herein, and can include any methods or compositions for adjusting or optimizing the invertase expression, as would be understood by a person skilled in the art. In some embodiments, the invertase expression associated with the exogenous invertase gene of the genetically modified yeast is not modified, i.e., the amino acid sequence of the invertase is the same or substantially the same to the unmodified invertase amino acid sequence.

In some embodiments, the yeast can be engineered for improved acetate consumption. Acetate consumption can be improved by overexpression of a gene encoding for an aldehyde dehydrogenase, or an acetyl-CoA synthase. In some embodiments, acetate consumption can be further improved by providing the cell with a greater pool of reducing equivalents to assist in the oxido-reduction of acetate to ethanol. One example of a genetic modification that can increase the pool of reducing equivalents is the deletion or disruption of a gene encoding a glycerol-3-phosphate dehydrogenase (GPD).

In some embodiments, the yeast can include heterologous expression of a transporter that can increase hexose uptake. An example of a transporter than can increase hexose uptake is Hxt1 transporter of *S. cerevisiae*. One skilled in the art would recognize that yeasts are known to have other transporters capable of hexose uptake.

In some embodiments, the yeast is capable of producing a fermentation product at a production rate of at least 0.5 grams per liter-hour (g $L^{-1}$ $h^{-1}$), at least 0.6 at least g $L^{-1}$ $h^{-1}$, at least 0.7 g $L^{-1}$ $h^{-1}$, at least 0.8 g $L^{-1}$ $h^{-1}$, at least 0.9 g $L^{-1}$ $h^{-1}$, at least 1.0 g $L^{-1}$ $h^{-1}$, at least 1.5 g $L^{-1}$ $h^{-1}$, or at least 2.0 g $L^{-1}$ $h^{-1}$. In some embodiments, the yeast is capable of producing a fermentation product at a pathway fermentation yield of at least 35 percent, at least 40 percent, at least 45 percent, or at least 50 percent. In some embodiments, the yeast is capable of producing a fermentation product at a final titer of at least 30 g/liter, at least 35 g/liter, at least 40 g/liter, at least 45 g/liter, at least 50 g/liter, at least 55 g/liter, at least 60 g/liter, at least 65 g/liter, at least 70 g/liter, at least 75 g/liter, at least 80 g/liter, at least 85 g/liter, at least 90 g/liter, at least 100 g/liter, or at least 100 g/liter. In some embodiments, the fermentation product is ethanol. For ethanol, the fermentation production rates, pathway fermentation yields, and final titers listed above are particularly relevant or useful for commercial processes where the fermentation substrate includes substantial amounts of sucrose and/or xylose.

The yeast can also be capable of producing a fermentation product using other fermentation substrates in addition to sucrose. In one embodiment, the yeast is capable of using a fermentation substrate that includes sucrose and glucose. In another embodiment, the yeast is capable of using a fermentation substrate that includes sucrose and a pentose, for example xylose. In yet another embodiment, the yeast is capable of using a fermentation substrate that includes sucrose, glucose, and xylose. In some embodiments, the yeast is capable of using a fermentation substrate that includes hydrozylates, for example hydrozylates of starch or lignocellulosic hydrozylates. In some embodiments, the yeast is capable of using a fermentation substrate that includes any mixture or combination of sucrose, glucose, fructose, xylose, hydrozylates of starch, or lignocellulosic hydrozylates. As would be understood by a person skilled in the art, the yeast can be used with a fermentation substrate that does not include sucrose.

In one embodiment, the yeast of the present invention can include one or more inducible promoters. For example, the yeast may include a promoter capable of turning off invertase expression after most or all of the sucrose in the fermentation substrate has been hydrolyzed. As a further example, the yeast may contain a promoter that is capable of down regulating after the dissolved oxygen is reduced below a threshold.

Fermentation Processes

The present invention also relates to processes for manufacturing a fermentation product. The fermentation processes includes the step of fermenting a substrate using the genetically engineered yeasts described herein. The fermentation process can also include other steps, as would be understood by a person skilled in the art. Non-limiting examples of additional process steps include maintaining the temperature of the fermentation broth within a predetermined range, adjusting the pH during fermentation, and isolating the fermentation product from the fermentation broth. In some embodiments, the fermentation process is a microaerobic process.

The fermentation processes of the present invention can be run using sucrose as a substrate, as a result of using genetically engineered yeasts having a functional invertase gene. The substrate of the fermentation process can also include other components in addition to sucrose. In one embodiment, the fermentation process substrate can also include glucose, xylose or other pentoses, fructose, hydrozylates of starch, lignocellulosic hydrozylates, or any combination thereof. As contemplated herein, the sucrose component of the substrate will be hydrolyzed into glucose and fructose via the activity of invertase and/or sucrase. Accordingly, in some embodiments, the fermentation substrate may not contain any sucrose because all of the sucrose may be hydrolyzed at some point during the process.

The fermentation process can be run under various conditions. In one embodiment, the fermentation temperature, i.e., the temperature of fermentation broth during processing, is ambient temperature. In some embodiments, the fermentation temperature is maintained within a predetermined range. For example, the fermentation temperature can be maintained in the range of 25 to 45° C., 20 to 40° C., or 33 to 38° C. However, the fermentation temperature is not limited to any specific range recited herein.

The fermentation process can be run within certain oxygen uptake rate (OUR) ranges. In some embodiments, the volumetric OUR of the fermentation process can be in the range of 0.5 to 40, 1 to 30, 3 to 20, or 5 to 16 mmol $O_2/(L \cdot h)$. In some embodiments, the specific OUR can be in the range of 0.2 to 13, 0.3 to 10, 1 to 7, or 2 to 6 mmol $O_2/(g$ cell dry weight$\cdot h)$. However, the volumetric or specific OURs of the fermentation process are not limited to any specific rates or ranges recited herein.

The fermentation process can be run at various cell concentrations. In some embodiments, the cell dry weight at the end of fermentation can be 1 to 20, 1 to 10, 2 to 8, or 2.5 to 6 g cell dry weight/L. Further, the pitch density or pitching rate of the fermentation process can vary. In some embodiments, the pitch density can be 0.05 to 5, 0.05 to 4, or 0.05 to 2 g cell dry weight/L.

In addition, the fermentation process can be associated with various characteristics, such as, but not limited to, fermentation production rate, pathway fermentation yield, and final titer. In some embodiments, these characteristics can be affected based on the selection of the yeast and/or genetic modification of the yeast used in the fermentation process. In some embodiments, these characteristics can be affected by adjusting the fermentation process conditions. In some embodiments, these characteristics can be adjusted via a combination of yeast selection or modification and the selection of fermentation process conditions.

In some embodiments, the fermentation production rate of the process is at least 0.5 grams per liter-hour (g $L^{-1}$ $h^{-1}$), at least 0.6 at least g $L^{-1}$ $h^{-1}$, at least 0.7 g $L^{-1}$ $h^{-1}$, at least 0.8 g $L^{-1}$ $h^{-1}$, at least 0.9 g $L^{-1}$ $h^{-1}$, at least 1.0 g $L^{-1}$ $h^{-1}$, at least 1.5 g $L^{-1}$ $h^{-1}$, or at least 2.0 g $L^{-1}$ $h^{-1}$. In some embodiments, the pathway fermentation yield of the process is at least 35 percent, at least 40 percent, at least 45 percent, or at least 50 percent. In some embodiments, the final titer of the process is at least 30 g/liter, at least 35 g/liter, at least 40 g/liter, at least 45 g/liter, or at least 50 g/liter. In some embodiments, the fermentation product is ethanol.

In some embodiments, the fermentation process can include sucrose as a substrate for only a portion of the process. For example, in one embodiment, the fermentation process can include the step of generating a yeast seed using sucrose as substrate, then running the full production batch with a hydrolysate, a hydrolysate supplemented with sucrose, or other substrate instead of sucrose. In one such embodiment, the fermentation process can be run as a sucrose-fed batch. Further, the fermentation process can be a batch process, continuous process, or semi-continuous process, as would be understood by a person skilled in the art.

In one aspect, the fermentation process is a process for producing ethanol from a substrate containing sucrose and/or other materials associated with the processing of sugar cane, for example, but not limited to, bagasse and molasses.

In some embodiments, the process includes the steps of growing yeast seed using any of the genetically modified yeasts described herein, and inoculating a pentose-containing fermentation substrate with the yeast seed. In such a process, additional sucrose can be added after inoculation to maximize the amount of ethanol produced.

Fermentation Products

The genetically engineered yeast of the present invention and the fermentation processes using the genetically engineered yeast can be used to manufacture a variety of compounds. In one embodiment, the fermentation product is ethanol. Other potential fermentation products that can be manufactured using the genetically engineered yeast include, but are not limited to: amino acids, organic acids, hydroxyl-organic acids, alcohols such as propanol or butanol, polyols, fatty acids, fatty acids such as methyl esters, monoacyl glycerides, diacyl glycerides, triacyl glycerides, and mixtures thereof. Exemplary organic acids or amino acids include lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, and acetic acid and derivatives thereof and salts thereof. It is contemplated herein that isolation of the desired fermentation product produced from the fermentation process can be achieved via techniques well known to those skilled in the relevant art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Example 1

Genetically Modified Yeast Strains

Strain 40

Strain 40, described in International Application No. PCT/US2016/045579, filed Aug. 4, 2016, is an evolved *Issatchenkia orientalis* host strain that has been enabled for ethanol production from cellulosic feed stock.

Strain 1-1

Strain 40 is grown for several rounds on 5-fluoroorotic acid (FOA) plates to identify a strain in which the URA3 marker has looped out. Resulting isolates are streaked for single colony isolation on YPD plates. A single colony is selected. Loss of the URA3 marker is verified by PCR. A PCR verified isolate is designated Strain 1-1.

Strains 1-2, 1-3, 1-4 and 1-5

Strain 1-1 is transformed with SEQ ID NO: 7. SEQ ID NO: 7 contains: i) an expression cassette for the selectable marker gene URA from *I. orientalis* (IoURA) flanked by LoxP sites; ii) an expression cassette for an invertase from *K. lactis* (KlINV), encoding the amino acid sequence SEQ ID NO: 1 expressed by the PDC promoter SEQ ID NO: 8; and iii) flanking DNA for targeted chromosomal integration into integration locus A. Transformants are selected on ScD-Uracil plates. Resulting transformants are streaked for single colony isolation on ScD-Uracil plates. A single colony is selected. Correct integration of SEQ ID NO: 7 into the selected colony is verified by PCR. PCR verified isolates are designated Strains 1-2, 1-3, 1-4 and 1-5.

Strains 1-6 and 1-7

Strain 1-1 is transformed with SEQ ID NO: 9. SEQ ID NO: 9 contains: i) an expression cassette for the selectable marker gene URA from *I. orientalis* (IoURA) flanked by LoxP sites; ii) an expression cassette for an invertase from *K. lactis* (KlINV), encoding the amino acid sequence SEQ ID NO: 1 expressed by the RPL16B promoter SEQ ID NO: 10; and iii) flanking DNA for targeted chromosomal integration into integration locus A. Transformants are selected on ScD-Uracil plates. Resulting transformants are streaked for single colony isolation on ScD-Uracil plates. A single colony is selected. Correct integration of SEQ ID NO: 9 into the selected colony is verified by PCR. PCR verified isolates are designated Strains 1-6 and 1-7.

Example 2

Shake Flask Examples

PCR verified isolates of the strains are streaked out for single colonies on YPD plates and incubated at 30° C. until single colonies are visible (1-2 days). A streak of colonies from the plate is used to inoculate Seed A 250-mL baffled flask containing 30 mL of Glucose Medium (Table 1). The Seed A flasks are incubated at 34° C. with shaking at 300 rpm for ~8 h. The $OD_{600}$ of the flask is measured and the Seed B 250-mL baffled flask containing 30 mL of Xylose Defined Medium (Table 2) is inoculated from the Seed A flasks to an initial $OD_{600}$ of 0.5. The Seed B flasks are incubated at 34° C. with shaking at 200 rpm overnight. Two production 125-mL baffled flasks, each containing 30 mL of the Xylose Defined Medium, are inoculated using the Seed B cell suspension to reach an initial $OD_{600}$ of 0.5. The production flasks are incubated at 34° C. with shaking at 125 rpm for ~100 h. Samples are withdrawn from the broth for analysis by high performance liquid chromatography as described in Example 4. The average values from the duplicate production flasks are presented in the tables below.

The media compositions and the methods for preparing them are adapted from Verduyn, et. al, 1992, Yeast 8, 501-517. The solution compositions for the media are listed in Tables 1 and 2. For sucrose fermentations, the glucose in the media described in Table 2 is replaced with an equal amount by weight of sucrose.

TABLE 1

Glucose Medium For Seed A

Pre-sterilization:

| | |
|---|---|
| DI water | Fill to 0.8 L |
| Glucose (anhydrous) | 130 g/L |
| MES (0.1M) | 19.5 g/L |
| 25X DMu3 Salts Solution (Table 3) | 40.0 ml/L |
| 15% Calcium Hydroxide | 1.3 mL/L |

Post-sterilization (add aseptically):

| | |
|---|---|
| 1:100 aqueous dilution of Lubrizol antifoam (Lubrizol Corp, part number BCC-627) | 1.5 mL/L |
| 1000X DM3 Vitamin Solution (Table 4) | 1.0 mL/L |

TABLE 1-continued

Glucose Medium For Seed A

| | |
|---|---|
| Fe, Cu, Zn Stock Solution (Table 5) | 9.0 mL/L |
| 1000X DM Trace Elements Solution (Table 9-9) | 1.0 mL/L |
| 50% w/v Glycerol | 0.2 mL/L |

Adjust final volume to 1 L

TABLE 2

Xylose Defined Medium For Seed B and Production flasks

Pre-sterilization:

| | |
|---|---|
| DI water | Fill to 0.8 L |
| Glucose (anhydrous) or Sucrose, as described in the example | 15 g/L |
| Xylose | 95 g/L |
| MES (0.1M) | 19.5 g/L |
| 25X DMu3 Salts Solution (Table 3) | 40.0 mL/L |
| Acetic acid (glacial) | 8.0 mL/L |
| 15% Calcium Hydroxide | 1.3 mL/L |

Post-sterilization (add aseptically):

| | |
|---|---|
| 1:100 aqueous dilution of Lubrizol antifoam (Lubrizol Corp, part number BCC-627) | 1.5 mL/L |
| 1000X DM3 Vitamin Solution (Table 4) | 1.0 mL/L |
| Fe, Cu, Zn Stock Solution (Table 5) | 9.0 mL/L |
| 1000X DM Trace Elements Solution (Table 9-9) | 1.0 mL/L |
| 50% Glycerol | 0.2 mL/L |

Adjust final volume to 1 L

TABLE 3

25X DMu3 Salts Solution

| | |
|---|---|
| Urea | 56.75 g/L |
| Potassium phosphate monobasic | 75.0 g/L |
| Magnesium sulphate heptahydrate | 25.0 g/L |
| Demineralized water | To 1000 mL |

TABLE 4

1000X DM3 Vitamin Solution

| | |
|---|---|
| Biotin (D–) | 0.5 g/L |
| Calcium D(+) pantothenate | 1.0 g/L |
| Nicotinic acid | 5.0 g/L |
| Myo-inositol (for microbiology) | 25.0 g/L |
| Thiamine hydrochloride | 1.0 g/L |
| Pyridoxine hydrochloride | 1.0 g/L |
| p-Aminobenzoic acid | 0.20 g/L |
| Demineralized water | To 1000 mL |

TABLE 5

Fe, Zn, Cu Stock Solution

| | |
|---|---|
| EDTA (Titriplex III ®) | 15.00 g/L |
| Zinc sulphate heptahydrate | 4.50 g/L |

TABLE 5-continued

Fe, Zn, Cu Stock Solution

| | |
|---|---|
| Copper(II)sulphate pentahydrate | 0.30 g/L |
| Iron sulphate heptahydrate | 3.00 g/L |
| Demineralized water | To 1000 mL |

Dissolve the EDTA and ZnSO$_4$ · 7H$_2$O in 750 ml of demineralized water and set the pH to 6.0 with NaOH. While maintaining the pH at 6.0, dissolve the CuSO$_4$ · 5H$_2$O and FeSO$_4$ · 7H$_2$O one by one. When dissolved, adjust the pH to 4.0 with 1M HCl and adjust the volume to 1 liter. Filter through a 0.2 micron filter to sterilize.

Example 3

Invertase Activity Evaluation

The capability of a cell to convert sucrose to glucose and fructose is evaluated by the following protocol. The strains are taken from a fresh YPD plate and used to inoculate 50 mL of YPD liquid media. The culture is allowed to grow at 30° C./250 rpm overnight (16 hours). Fresh cultures are inoculated to an OD$_{600}$=1.0 in 50 mL of YPD liquid media and allowed to grow at 30° C./250 rpm for 3 hours. The cells are harvested by centrifugation at 3,500 rpm for 4 minutes. The pellets are washed with 25 mL of water and centrifuged at 3,500 rpm for 4 minutes; this step is repeated 2 times. Washed cells are resuspended in 5 mL of water. 10 μL of cell suspension is incubated with 40 μL water, 250 μL of 0.2 M sodium acetate, pH 4.9 and 125 μL of 0.5 M sucrose for 10 min at 37° C. Samples are filtered through a 0.22 μm filter. The glucose released is immediately measured on a YS12950 (Xylem Inc.). The activity is expressed as grams of glucose released per gram of cell dry weight/hour. Assays are carried out in duplicate.

This assay is adapted from Silveira, M. C. F., Carvajal, E., Bon, E. P. S., Assay for in vivo yeast invertase activity using NaF (1996) Analytical Biochemistry, 238 (1), pp. 26-28, and Georis, I., Cassart, J. -P., Breunig, K. D., Vandenhaute, Glucose repression of the *Kluyveromyces lactis* invertase gene KlINV1 does not require Miglp (1999), Molecular and General Genetics 261(4-5):862-70.

Example 4

Analytical Methods

Extracellular metabolites are measured using HPLC. For quantitation of the analytes in the shake flask and fermentation samples, 25 μL of standard or sample is aspirated using a Hamilton Microlab Autodiluter. The standard or sample and 475 μL of diluent are dispensed into a vial (1:20 dilution). The diluent contains 50 mM H$_2$SO$_4$. The samples are filtered with a 0.45 μm Whatman filter and are analyzed using a Waters 2695 liquid chromatography system (Waters, Milford, Mass., USA) equipped with an automatic sampler, column heater, isocratic pump, refractive index or UV detector, and Empower 3 Software (Waters Corporation). Samples after dilution (20 μL) are injected onto in-line Bio-Rad 87H Column (Bio-Rad Laboratories, Inc.) and eluted with 10 mM sulfuric acid at 0.6 ml/min and 55° C. Glucose, xylose, arabitol, pyruvate/xylulose, xylitol, lactic, glycerol, and ethanol are detected with the refractive index detector while acetate is detected with the UV detector.

Oligomeric and monomeric sugars are measured using UPLC. For quantiation of these analytes in the shake flask and fermentation samples, samples are diluted with 50% acetonitrile:50% H$_2$O to the range of standard curve (approximately 0-5 g/L) created for each analyte. The samples are filtered with a 0.20 μm Whatman filter and are analyzed using a ACQUITY H-class UPLC system (Waters, Milford, Mass., USA) equipped with an automatic sampler, column heater, quaternary pump, evaporative light scattering detector, and Empower 3 Software (Waters Corporation). Samples after dilution (2 μL) are injected onto in-line BEH Amide column (Waters Corporation) and eluted with a gradient of 80% acetonitrile:20% water:0.2% NH$_4$OH to 30% acetonitrile:70% water:0.2% NH$_4$OH at 0.13 ml/min and 35° C. Glucose, xylose, and sucrose are detected by ELSD. Data analysis is done with a log-log linear curve (log concentration vs. log area).

TABLE 6

Ethanol titers for glucose fermentations
Fermentations start with 15 g/L glucose, 95 g/L xylose
and 0 g/L ethanol, and run as described in Example 2.

| Strain | Invertase Containing? | Invertase Promoter | 29 hour Glucose titer (g/L) | 29 hour Xylose titer (g/L) | 29 hour Ethanol titer (g/L) |
|---|---|---|---|---|---|
| 40 | No | none | 0 | 0.4 | 40.6 |
| 1-2 | Yes | PDC | 0 | 1.7 | 41.4 |
| 1-3 | Yes | PDC | 0 | 0.8 | 41.3 |
| 1-4 | Yes | PDC | 0 | 1.9 | 42.1 |
| 1-5 | Yes | PDC | 0 | 2.3 | 41.8 |
| 1-6 | Yes | RPL16B | 0 | 0.5 | 40.5 |
| 1-7 | Yes | RPL16B | 0 | 0.9 | 41.7 |

Table 6 shows that the strains having exogenous invertase genes perform at least as well as strains not having an invertase gene with respect to ethanol titer when run in a fermentation process using media that includes glucose, xylose, and acetate.

TABLE 7

Ethanol titers for sucrose fermentations and invertase activity values
Fermentations start with 15 g/L sucrose, 95 g/L xylose and
0 g/L ethanol, and run as described in Example 2.
Invertase activity is measured in YPD grown cultures.

| Strain | Invertase Containing? | Invertase Promoter | 29 hour Sucrose titer (g/L) | 29 hour Xylose titer (g/L) | 29 hour Ethanol titer (g/L) | Invertase Activity (g glucose released/ (g CDW *h)) |
|---|---|---|---|---|---|---|
| 40 | No | none | 12.6 | 0.4 | 34.6 | 0 |
| 1-2 | Yes | PDC | 0 | 0.0 | 39.3 | 57.75 |
| 1-3 | Yes | PDC | 0 | 0.0 | 40.4 | 50.46 |
| 1-4 | Yes | PDC | 0 | 0.8 | 41.0 | 60.50 |
| 1-5 | Yes | PDC | 0 | 0.4 | 40.9 | 53.75 |
| 1-6 | Yes | RPL16B | 0 | 0.4 | 39.7 | 5.84 |
| 1-7 | Yes | RPL16B | 0 | 0.2 | 40.1 | 5.54 |

Table 7 shows that the strains having exogenous invertase genes perform significantly better than strains not having an invertase gene with respect to ethanol titer when run in a fermentation process using media that includes sucrose, xylose, and acetate.

The disclosures of each and every patent, patent application, or publication cited herein are hereby incorporated by reference in their entirety. While this invention has been disclosed with reference to specific embodiments, other embodiments and variations of this invention may be devised by others skilled in the art without departing from the true spirit and scope of the invention. The appended claims are intended to be construed to include all such embodiments and variations.

The invention claimed is:

1. A genetically engineered yeast capable of manufacturing ethanol, comprising: a yeast having a functional heterologous invertase gene and a heterologous xylose isomerase gene, wherein the yeast is capable of producing ethanol at a rate of at least 07 g $L^{-1}h^{-1}$ and the genetically engineered yeast is engineered from a host yeast wherein the wild-type of the host yeast does not include a functional invertase gene.

2. The yeast of claim 1, wherein the yeast is capable of an ethanol production rate of at least 1.0 g $L^{-1}h^{-1}$.

3. The yeast of claim 1, wherein the yeast is capable of an ethanol production rate of at least 1.5 g $L^{-1}h^{-1}$.

4. The yeast of claim 1, wherein the yeast is capable of producing ethanol at a pathway fermentation yield of at least 40 percent.

5. The yeast of claim 1, wherein the yeast is capable of producing ethanol at a pathway fermentation yield of at least 45 percent.

6. The yeast of claim 1, wherein the yeast is capable of producing ethanol at a pathway fermentation yield of at least 50 percent.

7. The yeast of claim 1, wherein the yeast is capable of producing ethanol at a pathway fermentation yield in the range of 35-50 percent.

8. The yeast of claim 1, wherein the yeast is capable of producing ethanol at a final titer of at least 30. 35, 40, 45, 50, 55, 60, 65. 70, 75, 80, 85, 90, 95, or 100 g/liter.

9. The yeast of claim 1, wherein the host yeast is a yeast of the *Issatchenkia orientalis/Pichia fermentans* clade.

10. The yeast of claim 1, wherein the host yeast is *Issatchenkia orientails*.

11. The yeast of claim 1, wherein the yeast is Crabtree-negative.

12. The yeast of claim 1, wherein the functional invertase gene is selected from the group consisting of SEQ ID NO: 1; SEQ ID NO: 2; SEQ ID NO: 3; and SEQ ID NO: 4.

13. The yeast of claim 1, further comprising an exogenous or artificial promoter for the functional invertase gene.

14. The yeast of claim 13, wherein the promoter is selected from the group consisting of Pyruvate decarboxylase, Glyceraldehyde-3- phosphate dehydrogenase, Translational elongation factor, Transaldolase, RPL16B, 3-phosphoglycerate kinase, and Enolase.

15. A process for manufacturing ethanol comprising fermenting a substrate using the yeast of claim 1, wherein the substrate comprises sucrose and/or xylose.

16. The process of claim 15, wherein the substrate comprises sucrose.

17. The process of claim 15, wherein the substrate comprises xylose.

18. A process for manufacturing ethanol, comprising: consuming a substrate using a genetically engineered yeast, wherein the yeast comprises an exogenous invertase gene and an exogenous xylose isomerase gene, and the substrate comprises sucrose.

19. The process of claim 18, wherein the substrate further comprises a pentose.

20. The process of claim 18, wherein the yeast is a yeast of the *Issatchenkia orientaisl/Pichia fermentans* clade.

* * * * *

SEQUENCE LISTING

<160> NUMBER OF SEQ ID NOS: 10

<210> SEQ ID NO 1
<211> LENGTH: 609
<212> TYPE: PRT
<213> ORGANISM: Kluyveromyces lactis

<400> SEQUENCE: 1

Met Leu Lys Leu Leu Ser Leu Met Val Pro Leu Ala Ser Ala Ala Val
1               5                   10                  15

Ile His Arg Arg Asp Ala Asn Ile Ser Ala Ile Ala Ser Glu Trp Asn
            20                  25                  30

Ser Thr Ser Asn Ser Ser Ser Leu Ser Leu Asn Arg Pro Ala Val
        35                  40                  45

His Tyr Ser Pro Glu Glu Gly Trp Met Asn Asp Pro Asn Gly Leu Trp
    50                  55                  60

Tyr Asp Ala Lys Glu Glu Asp Trp His Ile Tyr Tyr Gln Tyr Tyr Pro
65                  70                  75                  80

Asp Ala Pro His Trp Gly Leu Pro Leu Thr Trp Gly His Ala Val Ser
                85                  90                  95

Lys Asp Leu Thr Val Trp Asp Glu Gln Gly Val Ala Phe Gly Pro Glu
            100                 105                 110

Phe Glu Thr Ala Gly Ala Phe Ser Gly Ser Met Val Ile Asp Tyr Asn
            115                 120                 125

Asn Thr Ser Gly Phe Phe Asn Ser Ser Thr Asp Pro Arg Gln Arg Val
        130                 135                 140

Val Ala Ile Trp Thr Leu Asp Tyr Ser Gly Ser Glu Thr Gln Gln Leu
145                 150                 155                 160

Ser Tyr Ser His Asp Gly Gly Tyr Thr Phe Thr Glu Tyr Ser Asp Asn
                165                 170                 175

Pro Val Leu Asp Ile Asp Ser Asp Ala Phe Arg Asp Pro Lys Val Phe
            180                 185                 190

Trp Tyr Gln Gly Glu Asp Ser Glu Ser Glu Gly Asn Trp Val Met Thr
        195                 200                 205

Val Ala Glu Ala Asp Arg Phe Ser Val Leu Ile Tyr Ser Ser Pro Asp
210                 215                 220

Leu Lys Asn Trp Thr Leu Glu Ser Asn Phe Ser Arg Glu Gly Tyr Leu
225                 230                 235                 240

Gly Tyr Asn Tyr Glu Cys Pro Gly Leu Val Lys Val Pro Tyr Val Lys
                245                 250                 255

Asn Thr Thr Tyr Ala Ser Ala Pro Gly Ser Asn Ile Thr Ser Ser Gly
            260                 265                 270

Pro Leu His Pro Asn Ser Thr Val Ser Phe Ser Asn Ser Ser Ser Ile
        275                 280                 285

Ala Trp Asn Ala Ser Ser Val Pro Leu Asn Ile Thr Leu Ser Asn Ser
290                 295                 300

Thr Leu Val Asp Glu Thr Ser Gln Leu Glu Glu Val Gly Tyr Ala Trp
305                 310                 315                 320

Val Met Ile Val Ser Phe Asn Pro Gly Ser Ile Leu Gly Gly Ser Gly
                325                 330                 335

Thr Glu Tyr Phe Ile Gly Asp Phe Asn Gly Thr His Phe Glu Pro Leu
            340                 345                 350

Asp Lys Gln Thr Arg Phe Leu Asp Leu Gly Lys Asp Tyr Tyr Ala Leu
        355                 360                 365

```
Gln Thr Phe Phe Asn Thr Pro Asn Glu Val Asp Val Leu Gly Ile Ala
        370                 375                 380
Trp Ala Ser Asn Trp Gln Tyr Ala Asn Gln Val Pro Thr Asp Pro Trp
385                 390                 395                 400
Arg Ser Ser Met Ser Leu Val Arg Asn Phe Thr Ile Thr Glu Tyr Asn
                405                 410                 415
Ile Asn Ser Asn Thr Thr Ala Leu Val Leu Asn Ser Gln Pro Val Leu
                420                 425                 430
Asp Phe Thr Ser Leu Arg Lys Asn Gly Thr Ser Tyr Thr Leu Glu Asn
                435                 440                 445
Leu Thr Leu Asn Ser Ser His Glu Val Leu Glu Phe Glu Asp Pro
    450                 455                 460
Thr Gly Val Phe Glu Phe Ser Leu Glu Tyr Ser Val Asn Phe Thr Gly
465                 470                 475                 480
Ile His Asn Trp Val Phe Thr Asp Leu Ser Leu Tyr Phe Gln Gly Asp
                485                 490                 495
Lys Asp Ser Asp Glu Tyr Leu Arg Leu Gly Tyr Glu Ala Asn Ser Lys
                500                 505                 510
Gln Phe Phe Leu Asp Arg Gly His Ser Asn Ile Pro Phe Val Gln Glu
                515                 520                 525
Asn Pro Phe Phe Thr Gln Arg Leu Ser Val Ser Asn Pro Pro Ser Ser
        530                 535                 540
Asn Ser Ser Thr Phe Asp Val Tyr Gly Ile Val Asp Arg Asn Ile Ile
545                 550                 555                 560
Glu Leu Tyr Phe Asn Asn Gly Thr Val Thr Ser Thr Asn Thr Phe Phe
                565                 570                 575
Phe Ser Thr Gly Asn Asn Ile Gly Ser Ile Ile Val Lys Ser Gly Val
                580                 585                 590
Asp Asp Val Tyr Glu Ile Glu Ser Leu Lys Val Asn Gln Phe Tyr Val
                595                 600                 605
Asp

<210> SEQ ID NO 2
<211> LENGTH: 532
<212> TYPE: PRT
<213> ORGANISM: Saccharomyces cerevisiae

<400> SEQUENCE: 2

Met Leu Leu Gln Ala Phe Leu Phe Leu Leu Ala Gly Phe Ala Ala Lys
1               5                   10                  15
Ile Ser Ala Ser Met Thr Asn Glu Thr Ser Asp Arg Pro Leu Val His
                20                  25                  30
Phe Thr Pro Asn Lys Gly Trp Met Asn Asp Pro Asn Gly Leu Trp Tyr
            35                  40                  45
Asp Glu Lys Asp Ala Lys Trp His Leu Tyr Phe Gln Tyr Asn Pro Asn
    50                  55                  60
Asp Thr Val Trp Gly Thr Pro Leu Phe Trp Gly His Ala Thr Ser Asp
65                  70                  75                  80
Asp Leu Thr Asn Trp Glu Asp Gln Pro Ile Ala Ile Ala Pro Lys Arg
                85                  90                  95
Asn Asp Ser Gly Ala Phe Ser Gly Ser Met Val Val Asp Tyr Asn Asn
                100                 105                 110
Thr Ser Gly Phe Phe Asn Asp Thr Ile Asp Pro Arg Gln Arg Cys Val
            115                 120                 125
```

```
Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Leu Lys Ser Trp Lys Leu
                195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530
```

```
<210> SEQ ID NO 3
<211> LENGTH: 581
<212> TYPE: PRT
<213> ORGANISM: Schizosaccharomyces pombe

<400> SEQUENCE: 3

Met Phe Leu Lys Tyr Ile Leu Ala Ser Gly Ile Cys Leu Val Ser Leu
1               5                   10                  15

Leu Ser Ser Thr Asn Ala Ala Pro Arg His Leu Tyr Val Lys Arg Tyr
            20                  25                  30

Pro Val Ile Tyr Asn Ala Ser Asn Ile Thr Glu Val Ser Asn Ser Thr
        35                  40                  45

Thr Val Pro Pro Pro Phe Val Asn Thr Thr Ala Pro Asn Gly Thr
    50                  55                  60

Cys Leu Gly Asn Tyr Asn Glu Tyr Leu Pro Ser Gly Tyr Tyr Asn Ala
65                  70                  75                  80

Thr Asp Arg Pro Lys Ile His Phe Thr Pro Ser Ser Gly Phe Met Asn
                85                  90                  95

Asp Pro Asn Gly Leu Val Tyr Thr Gly Val Tyr His Met Phe Phe
            100                 105                 110

Gln Tyr Ser Pro Lys Thr Leu Thr Ala Gly Glu Val Trp Gly His
        115                 120                 125

Thr Val Ser Lys Asp Leu Ile His Trp Glu Asn Tyr Pro Ile Ala Ile
130                 135                 140

Tyr Pro Asp Glu His Glu Asn Gly Val Leu Ser Leu Pro Phe Ser Gly
145                 150                 155                 160

Ser Ala Val Val Asp Val His Asn Ser Ser Gly Leu Phe Ser Asn Asp
                165                 170                 175

Thr Ile Pro Glu Glu Arg Ile Val Leu Ile Tyr Thr Asp His Trp Thr
            180                 185                 190

Gly Val Ala Glu Arg Gln Ala Ile Ala Tyr Thr Thr Asp Gly Gly Tyr
        195                 200                 205

Thr Phe Lys Lys Tyr Ser Gly Asn Pro Val Leu Asp Ile Asn Ser Leu
210                 215                 220

Gln Phe Arg Asp Pro Lys Val Ile Trp Asp Phe Asp Ala Asn Arg Trp
225                 230                 235                 240

Val Met Ile Val Ala Met Ser Gln Asn Tyr Gly Ile Ala Phe Tyr Ser
                245                 250                 255

Ser Tyr Asp Leu Ile His Trp Thr Glu Leu Ser Val Phe Ser Thr Ser
            260                 265                 270

Gly Tyr Leu Gly Leu Gln Tyr Glu Cys Pro Gly Met Ala Arg Val Pro
        275                 280                 285

Val Glu Gly Thr Asp Glu Tyr Lys Trp Val Leu Phe Ile Ser Ile Asn
    290                 295                 300

Pro Gly Ala Pro Leu Gly Gly Ser Val Val Gln Tyr Phe Val Gly Asp
305                 310                 315                 320

Trp Asn Gly Thr Asn Phe Val Pro Asp Asp Gly Gln Thr Arg Phe Val
                325                 330                 335

Asp Leu Gly Lys Asp Phe Tyr Ala Ser Ala Leu Tyr His Ser Ser Ser
            340                 345                 350

Ala Asn Ala Asp Val Ile Gly Val Gly Trp Ala Ser Asn Trp Gln Tyr
        355                 360                 365

Thr Asn Gln Ala Pro Thr Gln Val Phe Arg Ser Ala Met Thr Val Ala
    370                 375                 380
```

-continued

Arg Lys Phe Thr Leu Arg Asp Val Pro Gln Asn Pro Met Thr Asn Leu
385                 390                 395                 400

Thr Ser Leu Ile Gln Thr Pro Leu Asn Val Ser Leu Leu Arg Asp Glu
            405                 410                 415

Thr Leu Phe Thr Ala Pro Val Ile Asn Ser Ser Ser Leu Ser Gly
        420                 425                 430

Ser Pro Ile Thr Leu Pro Ser Asn Thr Ala Phe Glu Phe Asn Val Thr
        435                 440                 445

Leu Ser Ile Asn Tyr Thr Glu Gly Cys Thr Thr Gly Tyr Cys Leu Gly
    450                 455                 460

Arg Ile Ile Ile Asp Ser Asp Pro Tyr Arg Leu Gln Ser Ile Ser
465                 470                 475                 480

Val Asp Val Asp Phe Ala Ala Ser Thr Leu Val Ile Asn Arg Ala Lys
                485                 490                 495

Ala Gln Met Gly Trp Phe Asn Ser Leu Phe Thr Pro Ser Phe Ala Asn
            500                 505                 510

Asp Ile Tyr Ile Tyr Gly Asn Val Thr Leu Tyr Gly Ile Val Asp Asn
            515                 520                 525

Gly Leu Leu Glu Leu Tyr Val Asn Asn Gly Glu Lys Thr Tyr Thr Asn
530                 535                 540

Asp Phe Phe Leu Gln Gly Ala Thr Pro Gly Gln Ile Ser Phe Ala
545                 550                 555                 560

Ala Phe Gln Gly Val Ser Phe Asn Asn Val Thr Val Thr Pro Leu Lys
            565                 570                 575

Thr Ile Trp Asn Cys
            580

<210> SEQ ID NO 4
<211> LENGTH: 627
<212> TYPE: PRT
<213> ORGANISM: Aspergillus niger

<400> SEQUENCE: 4

Met His Ile Leu Pro Gly Ser Gln His Ala Ala Glu Leu Asp Asn Ser
1               5                   10                  15

Gly Thr Leu Ile His Ser Val His Cys Asp Pro Glu Gln Lys Ala Lys
            20                  25                  30

Asn Ile Pro Gln Ser Thr Gly Ile Ala Gln Ala Ser Ser Glu Trp Arg
        35                  40                  45

Pro Ser Tyr His Leu Ala Ala Pro Arg Gly Trp Met Asn Asp Pro Cys
    50                  55                  60

Gly Leu Gly Tyr Asp Pro Thr Thr Gly Leu Tyr His Leu Ser Phe Gln
65              70                  75                  80

Trp Asn Pro His Gly Asn Asp Trp Gly Asn Ile Ser Trp Gly His Ala
                85                  90                  95

Thr Ser Ser Asp Leu Val Ser Trp Gln Ile Ser Pro Glu Pro Cys Leu
            100                 105                 110

Thr Pro Ser Ala Glu Tyr Asp Arg Cys Gly Val Phe Thr Gly Cys Phe
        115                 120                 125

Arg Ser His Gly Pro Asp Gly Lys Pro Gly Val Leu Thr Tyr Val Tyr
    130                 135                 140

Thr Ser Val Asn His Leu Pro Leu His Tyr Thr Leu Pro Tyr Val Lys
145                 150                 155                 160

Gly Ser Glu Ser Leu Ser Ile Ala Val Ser Arg Asp His Gly Lys Thr
                165                 170                 175

-continued

```
Trp Gln Arg Ile Asp Ser Asn Pro Ile His Pro Gly Ala Pro Ala Gly
            180                 185                 190

Leu Glu Val Thr Gly Trp Arg Asp Pro Tyr Leu Asn Cys Trp Pro Ser
        195                 200                 205

Leu Arg Ala Gln Arg Gln Gly Val Ala Ser Pro Asp Leu Tyr Gly
    210                 215                 220

Phe Ile Ser Gly Gly Ile Ala Lys Glu Ser Pro Thr Val Phe Val Tyr
225                 230                 235                 240

Val Val Asn Pro Asp Asn Leu Thr Glu Trp Thr Tyr Ile Gly Pro Leu
            245                 250                 255

Leu His Val Gly Leu Asn Tyr Arg Pro Ser Arg Trp Ser Gly Asp Leu
        260                 265                 270

Gly Val Asn Trp Glu Val Ala Asn Phe Phe Thr Leu Thr Asp Gly Gly
    275                 280                 285

Val Ser Arg Asp Ile Val Ile Phe Gly Ala Glu Gly Cys Leu Ser Cys
    290                 295                 300

Glu Val Gly Ser Lys Arg Val Pro Arg Ser Leu Leu Trp Met Cys Ile
305                 310                 315                 320

Asn Val Arg Pro Gly Leu Gln Ala Gln Ser Ser Gly Glu Pro Leu Ala
            325                 330                 335

Asp Tyr Ser Phe Ser Gly Ile Phe Asp His Gly Cys Cys Tyr Ala Ala
        340                 345                 350

Asn Ser Phe Trp Asp Pro Val Thr Glu Tyr Val Val Tyr Cys Trp
    355                 360                 365

Ile Thr Glu Glu Asp Leu Pro Asp Arg Leu Arg His Arg Gln Gly Trp
    370                 375                 380

Ser Gly Ile Met Ser Leu Pro Arg Leu Val Arg Leu Val Thr Leu His
385                 390                 395                 400

Asn Val Lys Arg Ala His Gln Ser Lys Leu Glu Ser Ile Thr Ser Val
            405                 410                 415

Glu Ile Glu Arg His Ser Gln Gly Thr Gln Val Arg Thr Leu Ser Val
        420                 425                 430

Arg Pro Asp Pro Arg Leu Asn Ile Leu Arg Thr Ser Ala Arg Glu Leu
    435                 440                 445

His Leu Ser Asn Val Gln Leu Gly Ser Val Ala His Gln Pro Ala
450                 455                 460

Phe Leu Pro Leu Arg Thr Ala Arg Trp Glu Met Thr Ala Thr Phe Val
465                 470                 475                 480

Ile Gly Thr His Cys Ala Ala Val Gly Leu Glu Ile Gly His Ser Pro
            485                 490                 495

Asp Phe His Gln Arg Thr Thr Leu Ser Trp Ile Pro Tyr Asp Glu Thr
        500                 505                 510

Phe Thr Ile Glu Arg Pro Pro Leu His Asp Ala Gly Ile Asn His Val
    515                 520                 525

Pro Glu Thr Ala Pro His Thr Leu Phe Thr Phe Cys Asn Asn Glu Gly
    530                 535                 540

Glu Glu Val Thr Glu Pro Leu Gln Ile His Ala Tyr Phe Asp Ala Ser
545                 550                 555                 560

Val Leu Glu Val Phe Val Asn Ser Arg Thr Val Ile Ser Thr Arg Ile
            565                 570                 575

Tyr Thr Pro His Ala Gln Val Cys Thr Gly Leu Lys Phe Phe Ala Ser
        580                 585                 590
```

Ala Thr Glu Ser Gln Pro Lys Pro Ser Thr Ser Ala Pro Ala Ala Val
            595                 600                 605

Leu Val Arg Ala Asp Ile Trp Asp Gly Leu Ser Val Ile Arg Asp Glu
    610                 615                 620

Ile Lys His
625

<210> SEQ ID NO 5
<211> LENGTH: 1044
<212> TYPE: DNA
<213> ORGANISM: Issatchenkia orientalis

<400> SEQUENCE: 5

| | | | | | |
|---|---|---|---|---|---|
| cgctgcattc | gccacaacgt | cacgtgaggc | atcgtagttt | tgagtttttt | tttttttgata | 60 |
| aatctcgttt | cctgtgatat | gtttgccgtg | cgcctggtcg | attttcacct | tctttgaaat | 120 |
| ccgagttcgg | gaatgcaatt | gggaaaaagc | caaggagaaa | gaaaacaaaa | agagagttgc | 180 |
| gtagaaactc | ggaatgctcg | aagaaaccag | acagttgatg | gctggtttcc | gttttgagga | 240 |
| cgcttggtgt | gtgtaacttg | gatttgcaca | ctagagccgt | ctctgcattg | tattaaggtg | 300 |
| taaggacggt | gaatcatcgc | gatggagcgg | ggttttttct | tttggcaggt | ttttccgcgg | 360 |
| aaggcgagag | ggcggaaggg | ggggggtgt | atgtagttca | tatttcggca | ttactacaag | 420 |
| gatgtttccg | tacattgcat | ggtactgggg | ttctcctttt | cttgcacatc | tccataaact | 480 |
| aaatatcaat | agatgtatcc | gtttggaatc | tcatgacttt | tggtgtgtgg | tctgtgtctt | 540 |
| cccagttatc | tacttgagtg | attatgaacc | agttttcacc | attggttaca | taccaaacag | 600 |
| agaacttata | cgcaccagaa | cgccttttgt | gtcttttttgt | ttctcaagta | tttctatcag | 660 |
| tttccttcat | gtatcccggg | actccattgt | cctcggtagt | gcctaccaat | ttaatgtttg | 720 |
| actcctgcgt | tttctcctgt | cgcggacaaa | cggtgcggct | ccccgatga | ttcacgtaat | 780 |
| aagccggagt | caaccacaga | ggtcccctat | gactcaacaa | ggcctcgtag | aaactcggct | 840 |
| tctcggagaa | agagtctttt | cttttttcact | ggaaaatatt | ttttttttcc | tttatattct | 900 |
| tttgaaccaa | aatgtggcta | ctataaaagt | gcctttattc | cccagctttt | ctagcatgat | 960 |
| tgagtcacct | tccacaatga | gtcttctttg | ttgttagtat | tgtgaatatt | atccgtgcag | 1020 |
| ttttcaagaa | cgttaatcaa | catc | | | | 1044 |

<210> SEQ ID NO 6
<211> LENGTH: 561
<212> TYPE: DNA
<213> ORGANISM: Issatchenkia orientalis

<400> SEQUENCE: 6

| | | | | | |
|---|---|---|---|---|---|
| agttccgact | ggtgtttcgg | atgcctcttt | ttctaaggag | ctagattctg | gccccacact | 60 |
| agtctttgaa | ctcgttgctc | ccttaccacc | cttaccacca | gccttacttg | taggttttc | 120 |
| agtagcatac | tctgcgtgtt | tgactaaatt | cccttcctta | actttgtgcc | agcttggcca | 180 |
| tatcattaaa | tacccactga | aacttctaac | aactcttcga | ccttcctgat | gggcctttga | 240 |
| aattgtatct | accaaacctg | ccttcaaggg | atgttcttta | tatccctga | cgtctttcat | 300 |
| actttgaact | tcctctggga | cgtcttcctt | tccatatttt | tcccattggc | ccggcttgtt | 360 |
| tttagatttg | tctatctcac | ggaaaattga | ggggttcata | cttaatccac | tcacaccaac | 420 |
| cctgatgtta | gaagacagtt | ttgctaaatt | atttacattc | tgacttgtgt | ttgtcgatat | 480 |

```
aactgaatca gatggtttca tcgatgattc tcgggagact ggttctgatg gcgtcaccgg      540
ggtctcagat gctgctggat t                                                561

<210> SEQ ID NO 7
<211> LENGTH: 5979
<212> TYPE: DNA
<213> ORGANISM: Artificial Sequence
<220> FEATURE:
<223> OTHER INFORMATION: Sequence put together from multiple organisms:
      I. orientalis and K. lactis

<400> SEQUENCE: 7
cttcgctgca ttcgccacaa cgtcacgtga ggcatcgtag ttttgagttt tttttttttg       60
ataaatctcg tttcctgtga tatgtttgcc gtgcgcctgg tcgattttca ccttctttga      120
aatccgagtt cgggaatgca attgggaaaa agccaaggag aaagaaaaca aaagagagt       180 tgcgtagaaa ctcggaatgc tcgaagaaac agacagttg atggctggtt tccgttttga      240
ggacgcttgg tgtgtgtaac ttggatttgc acactagagc cgtctctgca ttgtattaag      300
gtgtaaggac ggtgaatcat cgcgatggag cggggttttt tcttttggca ggttttttccg     360 cggaaggcga gagggcggaa ggggggggg tgtatgtagt tcatatttcg gcattactac       420
aaggatgttt ccgtacattg catggtactg gggttctcct tttcttgcac atctccataa      480
actaaatatc aatagatgta tccgtttgga atctcatgac ttttggtgtg tggtctgtgt      540
cttcccagtt atctacttga gtgattatga accagttttc accattggtt acataccaaa      600
cagagaactt atacgcacca gaacgccttt tgtgtctttt tgtttctcaa gtatttctat      660
cagtttcctt catgtatccc gggactccat tgtcctcggt agtgcctacc aatttaatgt      720
ttgactcctg cgtttctcc tgtcgcggac aaacggtgcg gctccccga tgattcacgt       780 aataagccgg agtcaaccac agaggtcccc tatgactcaa caaggcctcg tagaaactcg      840
gcttctcgga gaaagagtct tttctttttc actggaaaat atttttttttt tcctttatat    900 tcttttgaac caaaatgtgg ctactataaa agtgccttta ttccccagct tttctagcat      960
gattgagtca ccttccacaa tgagtcttct ttgttgttag tattgtgaat attatccgtg     1020
cagttttcaa gaacgttaat caacatcggc cgcaatgtag aagggcgaat tcgcccttac     1080
atatgataac ttcgtataat gtatgctata cgaagttatc atagcctcat gaaatcagcc     1140
atttgctttt gttcaacgat cttttgaaat tgttgttgtt cttggtagtt aagttgatcc     1200
atcttggctt atgttgtgtg tatgttgtag ttattcttag tatattcctg tcctgagttt     1260
agtgaaacat aatatcgcct tgaaatgaaa atgctgaaat tcgtcgacat acaattttc     1320 aaactttttt tttttcttgg tgcacggaca tgttttaaa ggaagtactc tataccagtt      1380
attcttcaca aatttaattg ctggagaata gatcttcaac gctttaataa agtagtttgt     1440
ttgtcaagga tggcgtcata caaagaaaga tcagaatcac acacttcccc tgttgctagg     1500
agacttttct ccatcatgga ggaaaagaag tctaaccttt gtgcatcatt ggatattact     1560
gaaactgaaa agcttctctc tattttggac actattggtc cttacatctg tctagttaaa     1620
acacacatcg atattgtttc tgattttacg tatgaaggaa ctgtgttgcc tttgaaggag     1680
cttgccaaga aacataattt tatgattttt gaagatagaa aatttgctga tattggtaac     1740
actgttaaaa atcaatataa atctggtgtc ttccgtattg ccgaatgggc tgacatcact     1800
aatgcacatg gtgtaacggg tgcaggtatt gtttctggct tgaaggaggc agcccaagaa     1860
acaaccagtg aacctagagg tttgctaatg cttgctgagt tatcatcaaa gggttcttta    1920
```

```
gcatatggtg aatatacaga aaaaacagta gaaattgcta atctgataa agagtttgtc      1980 attggtttta ttgcgcaaca cgatatgggc ggtagagaag aaggttttga ctggatcatt    2040
atgactccag gggttggttt agatgacaaa ggtgatgcac ttggtcaaca atatagaact    2100
gttgatgaag ttgtaaagac tggaacggat atcataattg ttggtagagg tttgtacggt    2160
caaggaagag atcctataga gcaagctaaa agataccaac aagctggttg gaatgcttat    2220
ttaaacagat ttaaatgatt cttacacaaa gatttgatac atgtacacta gtttaaataa    2280
gcatgaaaag aattacacaa gcaaaaaaaa aaaataaat gaggtacttt acgttcacct     2340
acaaccaaaa aaactagata gagtaaaatc ttaagattta gaaaaagttg tttaacaaag    2400
gctttagtat gtgaattttt aatgtagcaa agcgataact aataaacata aacaaaagta    2460
tggttttctt tatcagtcaa atcattatcg attgattgtt ccgcgtatct gcagataact    2520
tcgtataatg tatgctatac gaagttatag atcgaattct tttattataa aattatatat    2580
tattcttaat tacatatcac ccttctatca gggaagggag aaacgaaaat agagagtgac    2640
ctatccaagc ttgggggtct aagttttaat ggcccaggga atcattactt ttttttctca    2700
atccttgatg gataaaagta ttacatacgt acaggattgt gtattagtgt atttcgttat    2760
atgattaaac aaagtttata gattgtaaag tagacgtaaa gtttagtaat tcattttaat    2820
gttcatttta cattcagatg ttaattaatt agtcaacgta aaactgatta accttcaatg    2880 attcaattte atagacgtca tcaacaccag acttaacaat gatggaacca atattgttac    2940
cagtggagaa gaaaaaggtg ttagtagagg taacagtacc attgttgaaa tacaattcaa    3000
tgatatttct gtcaacaata ccgtagacat cgaaggtgga ggagttggag gatggaggat    3060
tggaaactga aagtctctga gtgaagaatg gattttcttg aacaaatgga atgttagaat    3120
gacctctatc taaaaagaac tgcttggagt tagcttcgta accaagtctc aagtattcat    3180
ctgaatcctt atcaccttgg aaatacaagg acaagtcggt aaaaacccag ttgtgaatac    3240
cggtaaagtt gacggaatat tcaagggaaa attcgaaaac accggtagga tcttcaaatt    3300
ccaaaacctc gtgagaagag gagtttaatg taagattctc taagtatat gatgtgccgt     3360 tctttcttaa agaggtaaaa tctaaaactg gttgagagtt caagaccaat gcagtagtat    3420
tagaattgat gttgtattca gtgatagtga agtttctaac caaggacatg gatgatctcc    3480
atggatctgt tggaacttgg ttagcatatt gccaattaga ggcccatgcg atacccaaaa    3540
cgtcaacctc gtttgggta ttgaagaaag tttgcaaagc gtagtaatct ttacccaaat     3600
ctaagaatct agtttgctta tcaagtggct cgaagtgtgt accattaaag tcaccgatga    3660
agtattcagt accggaaccg cctaaaatgg agccaggatt gaatgagaca atcataaccc    3720
atgcgtaacc aacttcttcc aattgagaag tttcatcaac caaggtagaa ttggataaag    3780
taatgttaag tggaacggaa gaagcattcc atgcaataga ggatgaattt gagaaagaaa    3840
cagtagaatt tggatgaagt ggaccagatg aggtgatatt tgagcctgga gcagatgcgt    3900
atgtggtgtt tttgacgtat gggaccttaa ctaaaccagg acactcatag ttatagccta    3960
agtagccttc tctggaaaag tttgattcta aggtccaatt cttaaggtct ggagaagagt    4020
agattaagac ggagaaacga tctgcttcgg caactgtcat gacccagtta ccttctgatt    4080
cggaatcttc accttgatac cagaaaacct ttggatctct aaaagcgtct gagtcaatat    4140
ctaagacagg gttgtcagaa tattcggtga atgtataacc accatcatga gaataagata    4200
attgttgtgt ttcagagcca gaataatcca agtccaaat ggcaacgaca cgttgtcttg     4260
ggtcggtgga tgagttaaag aaaccggagg tgttattgta atcaataacc atagaaccag    4320
```

```
aaaaggcacc tgctgtttca aactctggac cgaatgcaac accttgttcg tcccagacgg    4380
tcaaatcttt ggagactgca tgaccccaag tcaatggcaa accccaatga ggggcatcag    4440
gatagtattg atagtagatg tgccaatctt cctctttagc atcgtaccat aaaccgtttg    4500
ggtcgttcat ccaaccttcc tctggagaat aatggacagc tggtctgttt aaagataaag    4560
atgaagaaga gttagaagtg gagttccatt cggatgcaat agctgaaatg ttagcatcac    4620
gtctgtggat aacagctgca gaagctaatg ggaccatcaa ggacaataac tttaacattt    4680
tatctagaat ttttgtgttt tgctgtgttt tgttttattt tgttttattg ggaagaaaat    4740
atataataat agaatattat atcaaaaaat aattaaagaa gctcaactgt ttttagaata    4800
aatgggttct ccgtgtcctt tttatacgcc ttctccgaaa agaaaaaaac catcgtatca    4860
tttgtagccc acgccacccg gaaaaaccac cattgtcctc agcagtccgc aaaaatatgg    4920
atgcgctcaa tcaatttccc tcccccgtca atgccaaaag gataacgaca cactattaag    4980
agcgcatcat ttgtaaaagc cgaggaaggg ggatacgctg accgagacgt ctcgcctcac    5040
tctcggagct gagccgccct ccttaagaaa ttcatggaga gaacacccct cgcggcttct    5100
gaacggctcg ccctcgtcca ttggtcacct cacagtggca actaataagg acattatagc    5160
aatagaaatt aaaatggtgc actgaaatac aataggatcg aataggatag gatacaataa    5220
gatacggaat attagactat actgtgatac ggtacgctac gatacgctac gatacgatac    5280
gatagaggat accacggata taacgtagtg ttattttttca ttattggggt tttttttctg    5340
tttgaatttt ccacgtcaag agtatcccat ctgacaggaa ccgatggact cctcgaggga    5400
tccgcggccg ctcagttccg actggtgttt cggatgcctc tttttctaag gagctagatt    5460
ctggccccac actagtcttt gaactcgttg ctcccttacc acccttacca ccagccttac    5520
ttgtaggttt tcagtagca tactctgcgt gtttgactaa attcccttcc ttaactttgt    5580
gccagcttgg ccatatcatt aaatacccac tgaaacttct aacaactctt cgaccttcct    5640
gatgggcctt tgaaattgta tctaccaaac ctgcctcaa gggatgttct ttatatcccc    5700
tgacgtcttt catactttga acttcctctg ggacgtcttc cttccatat ttttcccatt    5760 ggcccggctt gttttagat ttgtctatct cacggaaaat tgaggggttc atacttaatc    5820
cactcacacc aaccctgatg ttagaagaca gttttgctaa attatttaca ttctgacttg    5880
tgtttgtcga tataactgaa tcagatggtt tcatcgatga ttctcgggag actggttctg    5940
atggcgtcac cggggtctca gatgctgctg gattgggcc                          5979
```

<210> SEQ ID NO 8
<211> LENGTH: 703
<212> TYPE: DNA
<213> ORGANISM: Issatchenkia orientalis

<400> SEQUENCE: 8

```
gagtccatcg gttcctgtca gatgggatac tcttgacgtg gaaaattcaa acagaaaaaa     60
aaccccaata atgaaaaata acactacgtt atatccgtgg tatcctctat cgtatcgtat    120
cgtagcgtat cgtagcgtac cgtatcacag tatagtctaa tattccgtat cttattgtat    180
cctatcccta tcgatcctat tgtatttcag tgcaccattt taatttctat tgctataatg    240
tccttattag ttgccactgt gaggtgacca atggacgagg gcgagccgtt cagaagccgc    300
gaagggtgtt cttcccatga atttcttaag gagggcggct cagctccgag agtgaggcga    360
gacgtctcgt ttagcgtatc ccccttcctc ggcttttaca aatgatgcgc tcttaatagt    420
gtgtcgttat ccttttggca ttgacggggg agggaaattg attgagcgca tccatatttt    480
```

```
ggcggactgc tgaggacaat ggtggttttt ccgggtggcg tgggctacaa atgatacgat      540 ggttttttc ttttcggaga aggcgtataa aaaggacacg gagaacccat ttattctaat       600
aacagttgag cttctttaat tatttgttaa tataatattc tattattata tattttcttc      660
ccaataaaac aaaataaaac aaaacacagc aaaacacaaa aat                        703
```

<210> SEQ ID NO 9
<211> LENGTH: 6197
<212> TYPE: DNA
<213> ORGANISM: Artificial Sequence
<220> FEATURE:
<223> OTHER INFORMATION: Sequence put together from multiple organisms:
    I. orientalis and K. lactis <400> SEQUENCE: 9

```
cttcgctgca ttcgccacaa cgtcacgtga ggcatcgtag ttttgagttt ttttttttg        60 ataaatctcg tttcctgtga tatgtttgcc gtgcgcctgg tcgattttca ccttctttga     120
aatccgagtt cgggaatgca attgggaaaa agccaaggag aaagaaaaca aaagagagt      180 tgcgtagaaa ctcggaatgc tcgaagaaac cagacagttg atggctggtt ccgttttga     240 ggacgcttgg tgtgtgtaac ttggattgc acactagagc cgtctctgca ttgtattaag      300
gtgtaaggac ggtgaatcat cgcgatggag cggggttttt tcttttggca ggttttccg      360 cggaaggcga gagggcggaa gggggggggg tgtatgtagt tcatatttcg gcattactac      420
aaggatgttt ccgtacattg catggtactg gggttctcct tttcttgcac atctccataa     480
actaaatatc aatagatgta tccgtttgga atctcatgac ttttggtgtg tggtctgtgt      540
cttcccagtt atctacttga gtgattatga accagttttc accattggtt acataccaaa     600
cagagaactt atacgcacca gaacgccttt tgtgtctttt tgtttctcaa gtatttctat     660
cagtttcctt catgtatccc gggactccat tgtcctcggt agtgcctacc aatttaatgt     720
ttgactcctg cgtttttctcc tgtcgcggac aaacggtgcg gctccccga tgattcacgt     780 aataagccgg agtcaaccac agaggtcccc tatgactcaa caaggcctcg tagaaactcg     840
gcttctcgga gaaagagtct ttctttttc actggaaaat attttttttt tcctttatat     900
tcttttgaac caaaatgtgg ctactataaa agtgccttta ttccccagct tttctagcat     960
gattgagtca ccttccacaa tgagtcttct ttgttgttag tattgtgaat attatccgtg    1020
cagttttcaa gaacgttaat caacatcggc cgcaatgtag aagggcgaat cgcccttac    1080 atatgataac ttcgtataat gtatgctata cgaagttatc atagcctcat gaaatcagcc    1140
atttgctttt gttcaacgat cttttgaaat tgttgttgtt cttggtagtt aagttgatcc    1200
atcttggctt atgttgtgtg tatgttgtag ttattcttag tatattcctg tcctgagttt    1260
agtgaaacat aatatcgcct tgaaatgaaa atgctgaaat tcgtcgacat acaattttc     1320 aaactttttt tttttcttgg tgcacggaca tgttttaaa ggaagtactc tataccagtt    1380
attcttcaca aatttaattg ctggagaata gatcttcaac gctttaataa agtagtttgt    1440
ttgtcaagga tggcgtcata caaagaaaga tcagaatcac acacttcccc tgttgctagg    1500
agacttttct ccatcatgga ggaaaagaag tctaaccttt gtgcatcatt ggatattact    1560
gaaactgaaa agcttctctc tattttggac actattggtc cttacatctg tctagttaaa    1620
acacacatcg atattgtttc tgattttacg tatgaaggaa ctgtgttgcc tttgaaggag    1680
cttgccaaga aacataattt tatgattttt gaagatagaa aatttgctga tattggtaac    1740
actgttaaaa atcaatataa atctggtgtc ttccgtattg ccgaatgggc tgacatcact    1800
```

```
aatgcacatg gtgtaacggg tgcaggtatt gtttctggct tgaaggaggc agcccaagaa    1860
acaaccagtg aacctagagg tttgctaatg cttgctgagt tatcatcaaa gggttcttta    1920
gcatatggtg aatatacaga aaaaacagta gaaattgcta atctgataa agagtttgtc     1980 attggtttta ttgcgcaaca cgatatgggc ggtagagaag aaggttttga ctggatcatt    2040
atgactccag gggttggttt agatgacaaa ggtgatgcac ttggtcaaca atatagaact    2100
gttgatgaag ttgtaaagac tggaacggat atcataattg ttggtagagg tttgtacggt    2160
caaggaagag atcctataga gcaagctaaa agataccaac aagctggttg gaatgcttat    2220
ttaaacagat ttaaatgatt cttacacaaa gatttgatac atgtacacta gtttaaataa    2280
gcatgaaaag aattacacaa gcaaaaaaaa aaaataaat gaggtacttt acgttcacct     2340
acaaccaaaa aaactagata gagtaaaatc ttaagattta gaaaaagttg tttaacaaag    2400
gctttagtat gtgaattttt aatgtagcaa agcgataact aataaacata acaaaagta     2460 tggttttctt tatcagtcaa atcattatcg attgattgtt ccgcgtatct gcagataact    2520
tcgtataatg tatgctatac gaagttatag atcgaattct tttattataa aattatatat    2580
tattcttaat tacatatcac ccttctatca gggaagggag aaacgaaaat agagagtgac    2640
ctatccaagc ttgggggtct aagttttaat ggcccaggga atcattactt ttttttctca    2700
atccttgatg gataaaagta ttacatacgt acaggattgt gtattagtgt atttcgttat    2760
atgattaaac aaagtttata gattgtaaag tagacgtaaa gtttagtaat tcattttaat    2820
gttcatttta cattcagatg ttaattaatt agtcaacgta aaactgatta accttcaatg    2880
attcaatttc atagacgtca tcaacaccag acttaacaat gatggaacca atattgttac    2940
cagtggagaa gaaaaaggtg ttagtagagg taacagtacc attgttgaaa tacaattcaa    3000
tgatatttct gtcaacaata ccgtagacat cgaaggtgga ggagttggag gatgcgaggat    3060 tggaaactga aagtctctga gtgaagaatg gattttcttg aacaaatgga atgttagaat    3120
gacctctatc taaaaagaac tgcttggagt tagcttcgta accaagtctc aagtattcat    3180
ctgaatcctt atcaccttgg aaatacaagg acaagtcggt aaaaacccag ttgtgaatac    3240
cggtaaagtt gacggaatat tcaagggaaa attcgaaaac accggtagga tcttcaaatt    3300
ccaaaacctc gtgagaagag gagtttaatg taagattctc taaagtatat gatgtgccgt    3360
tctttcttaa agaggtaaaa tctaaaactg gttgagagtt caagaccaat gcagtagtat    3420
tagaattgat gttgtattca gtgatagtga agtttctaac caaggacatg gatgatctcc    3480
atggatctgt tggaacttgg ttagcatatt gccaattaga ggcccatgcg atacccaaaa    3540
cgtcaacctc gtttggggta ttgaagaaag tttgcaaagc gtagtaatct ttacccaaat    3600
ctaagaatct agtttgctta tcaagtggct cgaagtgtgt accattaaag tcaccgatga    3660
agtattcagt accggaaccg cctaaaatgg agccaggatt gaatgagaca atcataaccc    3720
atgcgtaacc aacttcttcc aattgagaag tttcatcaac caaggtagaa ttggataaag    3780
taatgttaag tggaacggaa gaagcattcc atgcaataga ggatgaattt gagaaagaaa    3840
cagtagaatt tggatgaagt ggaccagatg aggtgatatt tgagcctgga gcagatgcgt    3900
atgtggtgtt tttgacgtat gggaccttaa ctaaaccagg acactcatag ttatagccta    3960
agtagccttc tctggaaaag tttgattcta aggtccaatt cttaaggtct ggagaagagt    4020
agattaagac ggagaaacga tctgcttcgg caactgtcat gacccagtta ccttctgatt    4080
cggaatcttc accttgatac cagaaaaacct ttggatctct aaaagcgtct gagtcaatat    4140
ctaagacagg gttgtcagaa tattcggtga atgtataacc accatcatga gaataagata    4200
```

| | | | | |
|---|---|---|---|---|
| attgttgtgt | ttcagagcca | gaataatcca | aagtccaaat | ggcaacgaca cgttgtcttg | 4260 |
| ggtcggtgga | tgagttaaag | aaaccggagg | tgttattgta | atcaataacc atagaaccag | 4320 |
| aaaaggcacc | tgctgtttca | aactctggac | cgaatgcaac | accttgttcg tcccagacgg | 4380 |
| tcaaatcttt | ggagactgca | tgaccccaag | tcaatggcaa | accccaatga ggggcatcag | 4440 |
| gatagtattg | atagtagatg | tgccaatctt | cctctttagc | atcgtaccat aaaccgtttg | 4500 |
| ggtcgttcat | ccaaccttcc | tctggagaat | aatggacagc | tggtctgttt aaagataaag | 4560 |
| atgaagaaga | gttagaagtg | gagttccatt | cggatgcaat | agctgaaatg ttagcatcac | 4620 |
| gtctgtggat | aacagctgca | gaagctaatg | ggaccatcaa | ggacaataac tttaacattt | 4680 |
| tatctagata | ttgaatgtgt | ctacagaaca | aacagtaaaa | cctttaatc acaacttcca | 4740 |
| caaactgaat | tttcaatata | acaaatcttt | caatcaaatg | agaaaattga ccaccatcca | 4800 |
| cctccaagct | ctcacacgag | ggatcccctc | ggtgtccctc | tgcaaggggg agcccaggag | 4860 |
| gaggagcgag | gggcaaggga | tcgggcaacc | cgccctcggt | tcctcccaaa cagggagtcg | 4920 |
| cttcagcaga | cggcgcgcac | taaacacaat | atgtgcggtg | cgcgggtgtc attgggtagg | 4980 |
| ctgtccggga | tggcagtcac | acatgtctaa | tttaacatac | ggggctacta attaggaaat | 5040 |
| ttgatacgtt | aatttgatga | tatggggct | cagcaaaaaa | tgggaaagat tgagggaatt | 5100 |
| gtttgaatac | tttgacctaa | tttacagaaa | aaacacgata | agataagcat ggggagactc | 5160 |
| ggaactcact | tatataggag | attattttgc | atttaaaaac | acatcaatgt catcataaat | 5220 |
| ggaatctatc | tgcacattgt | ctccatctat | gaggatctgg | ttgtccatca tattccgtaa | 5280 |
| aaggctgctt | acacgatgta | aaccaatcga | ctgtcgaggt | ttgcgttgtg taatctatat | 5340 |
| atatatatat | gtatggattg | gataatggca | atgttagtat | ttggaaagac acaatgtaaa | 5400 |
| acagtaatgc | atacatacaa | taacagttgt | taaatggttc | tgggatatat ctctgatatg | 5460 |
| tttgatgatt | tcaatcatta | ttcgaccagc | tgtcagttgg | aggcacaatg ttagtacaca | 5520 |
| tattcggatt | cgctaattgt | ccatggctat | tgtgttacct | acactttctc tggtcttcaa | 5580 |
| acatggagac | attgaatgcc | tcatccaaac | tcgagggatc | cgcggccgct cagttccgac | 5640 |
| tggtgtttcg | gatgcctctt | tttctaagga | gctagattct | ggcccacac tagtctttga | 5700 |
| actcgttgct | cccttaccac | ccttaccacc | agccttactt | gtaggttttt cagtagcata | 5760 |
| ctctgcgtgt | ttgactaaat | tcccttcctt | aactttgtgc | cagcttggcc atatcattaa | 5820 |
| atacccactg | aaacttctaa | caactcttcg | accttcctga | tgggcctttg aaattgtatc | 5880 |
| taccaaacct | gccttcaagg | gatgttcttt | atatccctg | acgtctttca tactttgaac | 5940 |
| ttcctctggg | acgtcttcct | ttccatattt | ttcccattgg | cccggcttgt ttttagattt | 6000 |
| gtctatctca | cggaaaattg | aggggttcat | acttaatcca | ctcacaccaa ccctgatgtt | 6060 |
| agaagacagt | tttgctaaat | tatttacatt | ctgacttgtg | tttgtcgata taactgaatc | 6120 |
| agatggtttc | atcgatgatt | ctcgggagac | tggttctgat | ggcgtcaccg gggtctcaga | 6180 |
| tgctgctgga | ttgggcc | | | | 6197 |

<210> SEQ ID NO 10
<211> LENGTH: 921
<212> TYPE: DNA
<213> ORGANISM: Issatchenkia orientalis

<400> SEQUENCE: 10

| | | | | | |
|---|---|---|---|---|---|
| tttggatgag | gcattcaatg | tctccatgtt | tgaagaccag | agaaagtgta ggtaacacaa | 60 |
| tagccatgga | caattagcga | atccgaatat | gtgtactaac | attgtgcctc caactgacag | 120 |

-continued

```
ctggtcgaat aatgattgaa atcatcaaac atatcagaga tatatcccag aaccatttaa    180
caactgttat tgtatgtatg cattactgtt ttacattgtg tctttccaaa tactaacatt    240
gccattatcc aatccataca tatatatata tatagattac acaacgcaaa cctcgacagt    300
cgattggttt acatcgtgta agcagccttt tacggaatat gatggacaac cagatcctca    360
tagatggaga caatgtgcag atagattcca tttatgatga cattgatgtg tttttaaatg    420
caaaataatc tcctatataa gtgagttccg agtctcccca tgcttatctt atcgtgtttt    480
ttctgtaaat taggtcaaag tattcaaaca attccctcaa tctttcccat tttttgctga    540
gcccccatat catcaaatta acgtatcaaa tttcctaatt agtagcccg tatgttaaat     600 tagacatgtg tgactgccat cccggacagc ctacccaatg acacccgcgc accgcacata    660
ttgtgtttag tgcgcgccgt ctgctgaagc gactccctgt ttgggaggaa ccgagggcgg    720
gttgcccgat cccttgcccc tcgctcctcc tcctgggctc ccccttgcag agggacaccg    780
aggggatccc tcgtgtgaga gcttggaggt ggatggtggt caattttctc atttgattga    840
aagatttgtt atattgaaaa ttcagtttgt ggaagttgtg attaaaaggt tttactgttt    900
gttctgtaga cacattcaat a                                              921
```